(12) United States Patent
Gilman et al.

(10) Patent No.: US 12,254,970 B2
(45) Date of Patent: *Mar. 18, 2025

(54) SYSTEMS AND METHODS FOR A NUMERIC WAITING BIN FOR PRESCRIPTION FULFILLMENT

(71) Applicant: CVS Pharmacy, Inc., Woonsocket, RI (US)

(72) Inventors: Nathaniel D. Gilman, Groton, CT (US); Christopher J. Goody, Mapleville, RI (US); Kyle J. McGrath, Kingstown, RI (US); Jeffrey Swindling, Smithfield, RI (US); Jared P. Tancrelle, Smithfield, RI (US); Li Mei Zhang, Dedham, MA (US)

(73) Assignee: CVS Pharmacy, Inc., Woonsocket, RI (US)

( * ) Notice: Subject to any disclaimer, the term of this patent is extended or adjusted under 35 U.S.C. 154(b) by 56 days.

This patent is subject to a terminal disclaimer.

(21) Appl. No.: 18/312,266

(22) Filed: May 4, 2023

(65) Prior Publication Data

US 2023/0274810 A1     Aug. 31, 2023

Related U.S. Application Data

(62) Division of application No. 16/588,272, filed on Sep. 30, 2019, now Pat. No. 11,798,668.

(Continued)

(51) Int. Cl.
*G16H 20/13* (2018.01)
*A61J 1/00* (2023.01)
(Continued)

(52) U.S. Cl.
CPC ............... *G16H 20/13* (2018.01); *A61J 1/00* (2013.01); *G06F 3/0482* (2013.01);
(Continued)

(58) Field of Classification Search
CPC ......... G16H 20/13; A61J 1/00; A61J 2205/30; A61J 2205/50; G06F 3/0482; G06Q 10/087
(Continued)

(56) References Cited

U.S. PATENT DOCUMENTS 2,699,254 A    1/1955  Bok
4,814,592 A    3/1989  Bradt
(Continued)

FOREIGN PATENT DOCUMENTS

| CA | 2699254 C | 12/2013 |
| JP | 5212649 B2 | 4/1977 |
| WO | 2008157632 A2 | 12/2008 |

*Primary Examiner* — Jacob K Ackun

(74) *Attorney, Agent, or Firm* — Patent Law Works LLP

(57) ABSTRACT

Systems and methods are disclosed for a numeric waiting bin for prescription fulfillment. A computing system may be used to receive bin configuration values corresponding to a plurality of physical bins for prescription storage. The bin configuration values may be used to assign serial identifiers to the plurality of bins. Prescriptions may be selectively assigned a bin serial identifier using a plurality of rules and the bin serial number may be used to locate the prescription when the prescription is requested, such as during pickup.

20 Claims, 10 Drawing Sheets

Related U.S. Application Data

(60) Provisional application No. 62/740,025, filed on Oct. 2, 2018.

(51) Int. Cl.
*G06F 3/0482* (2013.01)
*G06Q 10/087* (2023.01)

(52) U.S. Cl.
CPC ......... *G06Q 10/087* (2013.01); *A61J 2205/30* (2013.01); *A61J 2205/50* (2013.01)

(58) Field of Classification Search
USPC ........................................................ 206/438
See application file for complete search history.

(56) References Cited

U.S. PATENT DOCUMENTS

| | | |
|---|---|---|
| 4,839,505 A | 6/1989 | Bradt |
| 5,013,897 A | 5/1991 | Harman |
| 5,077,462 A | 12/1991 | Newell |
| 5,159,560 A | 10/1992 | Newell |
| 5,208,762 A | 5/1993 | Charhut |
| 5,212,649 A | 5/1993 | Pelletier |
| 5,337,920 A | 8/1994 | Clausen |
| 5,343,403 A | 8/1994 | Beidle |
| 5,438,523 A | 8/1995 | Humm |
| 5,597,995 A | 1/1997 | Williams |
| 5,839,257 A | 11/1998 | Soderstrom |
| 6,464,142 B1 | 10/2002 | Denenberg |
| 6,505,754 B1 | 1/2003 | Kenny |
| 6,587,031 B1 | 7/2003 | Daugherty |
| 7,854,332 B1 | 12/2010 | Clausen |
| 7,857,161 B2 | 12/2010 | Pinney |
| 7,860,724 B2 | 12/2010 | Chudy |
| 7,987,020 B1 | 7/2011 | Swinea, Jr. |
| 8,538,581 B2 | 9/2013 | Kuehnrich |
| 9,978,110 B2 | 5/2018 | Vahlberg |
| 10,198,547 B2 | 2/2019 | Hayashi |
| 10,319,173 B2 | 6/2019 | Adelberg |
| 11,798,668 B1 * | 10/2023 | Gilman ................. G06F 3/0482 |

* cited by examiner

SYSTEMS AND METHODS FOR A NUMERIC WAITING BIN FOR PRESCRIPTION FULFILLMENT

BACKGROUND

Current processes fulfillment of prescriptions for medication is a process that includes many highly manual and inefficient steps.

Today, the Waiting Bin is sorted in alphabetical order and it is up to each individual store team to determine the alphabetical labelling and the organization. This has resulted in uneven distribution of prescription storage causing overflow in some slots, underutilization of others, and increasing the time required to retrieve a prescription as part of the Pick-Up process. Additionally, prescriptions may have multiple types of storage requirements that are not readily intuitive to pharmacy colleagues, which may also increase the time to retrieve a prescription.

SUMMARY

Various aspects for configuring and managing pharmacy waiting bins for prescription fulfilment, particularly, numeric waiting bins that are automatically allocated by a numeric waiting bin engine are described.

One general aspect includes a system that includes a plurality of physical bins configured to receive and store prescriptions for customer pick-up and a computing system. The computing system also includes at least one processor, at least one memory, and a numeric waiting bin engine stored in the at least one memory and executable by the at least one processor. The numeric waiting bin engine is executable to: receive a plurality of bin configuration values, where the bin configuration values include a number of bins value and a preferred capacity value; store the plurality of bin configuration values in a bin configuration file in non-volatile storage; assign a plurality of serial identifiers to the plurality of physical bins using the bin configuration values, where each physical bin of the plurality of physical bins receives a unique serial identifier from the plurality of serial identifiers; selectively assign a slot serial identifier from the plurality of serial identifiers to a selected prescription, where the selected prescription has a size value and the size value is less than the preferred capacity value; and display, responsive to a request for the selected prescription, the slot serial identifier for the selected prescription on a graphical user interface of the computing system.

Implementations may include one or more of the following features. The computing system may further include a label printer for prescriptions. The numeric waiting bin engine may be further executable to transmit the slot serial identifier for the selected prescription to the label printer. The label printer may be configured to print the slot serial identifier on a prescription label affixed to the selected prescription. The computing system may further include a prescription management system. The numeric waiting bin engine may be further executable to transmit the slot serial identifier for the selected prescription to the prescription management system, where the prescription management system stores the slot serial identifier in a prescription record for the selected prescription. The numeric waiting bin engine may be further executable to store the slot serial identifier for the selected prescription in a prescription record for the selected prescription. The computing system may further include a point of sale system configured to: receive the request for the selected prescription; access the prescription record for the selected prescription; determine the slot serial identifier from the prescription record; and display the slot serial identifier for the selected prescription on a graphical user interface of the point of sale system. The bin configuration values may further include a stretch capacity value. The numeric waiting bin engine may be further executable to selectively assign the slot serial identifier from the plurality of serial identifiers to the selected prescription, where the size value of the selected prescription exceeds the preferred capacity value and does not exceed the stretch capacity value. The plurality of physical bins may include an oversized area for bulk storage. The bin configuration values may further include a bulk capacity value. The numeric waiting bin engine may be further executable to selectively assign the slot serial identifier from the plurality of serial identifiers to the selected prescription, where the size value of the selected prescription exceeds the bulk capacity value. The selected prescription may have an associated drug classification identifier. The associated drug classification identifier may indicate at least one special handling category selected from: refrigerate, reconstitute, immunization, controlled, and excluded. The numeric waiting bin engine may be further executable to selectively assign the slot serial identifier from the plurality of serial identifiers to the selected prescription using at least one fixed slot serial identifier corresponding to a storage location based on the associated drug classification identifier. The plurality of physical bins may include a plurality of sets of bins having different sizes. The bin configuration values may include a plurality of bin configuration sets, each bin configuration set of the plurality of bin configuration sets may correspond to a set of bins of equal size from the plurality of sets of bins, and each bin configuration set may include the number of bins value and the preferred capacity value for the corresponding set of bins of equal size. The numeric waiting bin engine may be further executable to selectively assign the slot serial identifier from the plurality of serial identifiers to the selected prescription, where the size value of the selected prescription exceeds the preferred capacity value of a first bin configuration set and does not exceed the preferred capacity value of a second bin configuration set, the slot serial identifier associated with a bin corresponding to the second bin configuration set. The computing system may further include a bin log file, the bin log file including prescription identifiers and size values for each serial identifier from the plurality of serial identifiers with at least one assigned prescription. The numeric waiting bin engine may be further executable to: access, responsive to a prescription fulfillment workflow, the bin log file; and process the bin log file using the size value to determine available slots from the plurality of serial identifiers with at least one assigned prescription, where the slot serial identifier is selectively assigned from the available slots. The numeric waiting bin engine may be further executable to: add, responsive to no slots from the plurality of serial identifiers with at least one assigned prescription accommodating the selected prescription, a new serial identifier for a next sequential bin not exceeding the number of bins value; and selectively assign the new serial identifier as the slot serial identifier for the selected prescription. The computing system may further include a rules engine configured to process a plurality of logical rules for selectively assigning the slot serial identifier to the selected prescription. The numeric waiting bin engine may be further executable to: evaluate, responsive to a prescription fulfillment workflow, a plurality of assignment rules using the rules engine and at least one value from a prescription record for the selected prescription; and determine, responsive to evaluating the plurality of assignment rules, the slot serial identifier to be selectively assigned to the selected prescription. The plurality of assignment rules may be selected from predetermined assignment rules, slot availability checking rules, capacity checking rules, bin generation rules, and bin recovery rules. The plurality of assignment rules may include grouping logic rules and evaluating the plurality of assignment rules may include: identifying a plurality of related prescriptions, including the selected prescription; evaluating at least one grouping logic rule to determine whether the plurality of related prescriptions may be assigned to the slot serial identifier; and evaluating at least one grouping logic rule to determine whether the plurality of related prescriptions may be assigned to a sequential set of serial identifiers including the slot serial identifier. Determining the slot serial identifier may include locating the plurality of related prescriptions as a group in the plurality of physical bins.

Another general aspect includes a computer-based method including: receiving, through a computer interface of a computing system, a plurality of bin configuration values corresponding to a plurality of physical bins, where the bin configuration values includes a number of bins value and a preferred capacity value; storing the plurality of bin configuration values in a bin configuration file in non-volatile storage of the computing system; assigning a plurality of serial identifiers to the plurality of physical bins using the bin configuration values, where each physical bin of the plurality of physical bins receives a unique serial identifier from the plurality of serial identifiers; selectively assigning a slot serial identifier from the plurality of serial identifiers to a selected prescription, where the selected prescription has a size value and the size value is less than the preferred capacity value; and displaying, responsive to a request for the selected prescription, the slot serial identifier for the selected prescription on a graphical user interface of the computing system.

Implementations may include one or more of the following features. The computer-based method may further include: transmitting the slot serial identifier for the selected prescription to a label printer of the computing system; and printing, using the label printer, the slot serial identifier on a prescription label affixed to the selected prescription. The computer-based method may further include: storing, by a pharmacy management system connected to the computing system, the slot serial identifier for the selected prescription in a prescription record for the selected prescription; receiving the request for the selected prescription at a point of sale system connected to the computing system; accessing the prescription record for the selected prescription from the pharmacy management system; determining the slot serial identifier from the prescription record; and displaying the slot serial identifier for the selected prescription on a graphical user interface of the point of sale system. The computer-based method may further include: receiving, through the computer interface of the computing system, a stretch capacity value from the bin configuration values; evaluating whether the size value exceeds the preferred capacity value of available slots of the plurality of serial identifiers; evaluating, responsive to determining the size value does exceed the preferred capacity value of available slots of the plurality of serial identifiers, whether the size value exceeds the stretch capacity value; selecting, responsive to determining the size value does not exceed the stretch capacity value, the slot serial identifier. The computer-based method may further include: determining an associated drug classification identifier for the selected prescription, where the associated drug classification identifier indicates at least one special handling category selected from: refrigerate, reconstitute, immunization, controlled, and excluded; and selecting the slot serial identifier from the plurality of serial identifiers for the selected prescription using at least one fixed slot serial identifier corresponding to a storage location based on the associated drug classification identifier. The computer-based method may further include: receiving, through the computer interface of the computing system, a plurality of bin configuration sets, where each bin configuration set of the plurality of bin configuration sets corresponds to a set of physical bins of equal size from the plurality of physical bins and each bin configuration set includes the number of bins value and the preferred capacity value for the corresponding set of bins of equal size; evaluating whether the size value exceeds the preferred capacity value of available slots of a first bin configuration set; evaluating, responsive to determining the size value does exceed the preferred capacity value of available slots of the first bin configuration set, whether the size value exceeds the preferred capacity value of available slots of a second bin configuration set; and selecting, responsive to determining the size value does not exceed the preferred capacity value of available slots of the second bin configuration set, the slot serial identifier from the second bin configuration set. The computer-based method may further include: storing a bin log file in the computer system, where the bin log file includes prescription identifiers and size values for each serial identifier from the plurality of serial identifiers with at least one assigned prescription; accessing, responsive to a prescription fulfillment workflow, the bin log file; and processing the bin log file using the size value to determine available slots from the plurality of serial identifiers with at least one assigned prescription, where the slot serial identifier is selectively assigned from the available slots. The computer-based method may further include: adding, responsive to no slots from the plurality of serial identifiers with at least one assigned prescription accommodating the selected prescription, a new serial identifier for a next sequential bin not exceeding the number of bins value; and selecting the new serial identifier as the slot serial identifier for the selected prescription. The computer-based method may further include: evaluating, using a rules engine to process a plurality of logical rules for selectively assigning the slot serial identifier to the selected prescription, a plurality of assignment rules using at least one value from a prescription record for the selected prescription; and selecting, responsive to evaluating the plurality of assignment rules, the slot serial identifier to be selectively assigned to the selected prescription, where the plurality of assignment rules is selected from predetermined assignment rules, slot availability checking rules, capacity checking rules, bin generation rules, bin recovery rules, and grouping logic rules.

Another general aspect includes a computing system including: at least one processor; at least one memory; non-volatile storage storing a plurality of bin configuration values corresponding to a plurality of physical bins configured to receive and store prescriptions for customer pick-up, where the bin configuration values include a number of bins value, a preferred capacity value; and a stretch capacity value; and a numeric waiting bin engine stored in the at least one memory and executable by the at least one processor. The numeric waiting bin engine is executable to: assign a plurality of serial identifiers to the plurality of physical bins using the bin configuration values, where each physical bin of the plurality of physical bins receives a unique serial identifier from the plurality of serial identifiers; evaluate, using a rules engine to process a plurality of logical rules for selectively assigning a slot serial identifier to a selected prescription, a plurality of assignment rules based on the preferred capacity value and the stretch capacity value; select, responsive to evaluating the plurality of assignment rules, the slot serial identifier for the selected prescription; and display, responsive to a request for the selected prescription, the slot serial identifier for the selected prescription on a graphical user interface of the computing system. The various embodiments advantageously apply the teachings of prescription and pharmacy management data systems to improve the functionality of such computer systems. The various embodiments include operations to overcome or at least reduce the issues in the previous prescription management systems discussed above and, accordingly, are more reliable and/or efficient than other pharmacy computing and prescription fulfilment system. That is, the various embodiments disclosed herein include hardware and/or software with functionality to improve the automated allocation of waiting bin space configured for each pharmacy location, such as by using a numeric waiting bin model and rules-based allocation of waiting bin slots to generate labels and display indicators for locating selected prescriptions in the waiting bins. Accordingly, the embodiments disclosed herein provide various improvements to storage networks and/or storage systems.

It should be understood that language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

As set forth in detail below, the technology described herein provides an innovative approach to deliver improved customer satisfaction and operating efficiency by integrating a computing system into the dynamic management of physical waiting bins.

One identified solution to reduce transaction time is a numeric waiting bin, that is, waiting bins that are assigned serial identifiers to describe their physical position or location, generally using a sequential numeric identifier. Filled prescriptions that have yet to be sold are stored in the waiting bin prior to customers picking up and the waiting bin identifier is used to locate the bin containing the prescription.

Previously, waiting bins were typically sorted in alphabetical order and it was up to each individual store team to determine the alphabetical labelling and the organization. This has resulted in uneven distribution of prescription storage causing overflow in some slots, underutilization of others, and increasing the time required to retrieve a prescription as part of the Pick-Up process. In addition, prescriptions may be dispensed in vials or containers of different sizes, such as 13, 16 or 20 dram vials. The use of larger containers may increase the space occupied per prescription leading to increased risk of overflow.

In some pharmacies, there may be no procedures in place to effectively manage the waiting bin as a whole. In larger retail pharmacy chains, individual retail stores may be evaluated individually by the Pharmacy Managers and District Leaders resulting in potentially different waiting bin processes for each store.

A numeric waiting bin system may systematically assign prescriptions a slot number in the waiting bin and effectively manage the number of prescriptions in each slot. The number may display on the label and on point of sale (POS) register screen to increase retrieval efficiency. The logic behind waiting bin assignments may be standardized and maintained at a corporate level and administered through enterprise prescription and pharmacy management systems. However, because individual stores may not have standard physical waiting bin areas, the numeric waiting bin engine may be configured (and reconfigured for changes in physical waiting bin space) using a simple set of bin configuration parameters, such as the number and size of the physical bins being used.

With reference to the figures, reference numbers may be used to refer to components found in any of the figures, regardless whether those reference numbers are shown in the figure being described. Further, where a reference number includes a decimal referring to one of multiple similar components (e.g., component 000.1, 000.2, and 000.n), the reference number may be used without the decimal to refer to one or all of the similar components. Note that decimal reference numbers may also be used for functionally distinct subcomponents, as will be clear from the associated written description.

Figure 1:
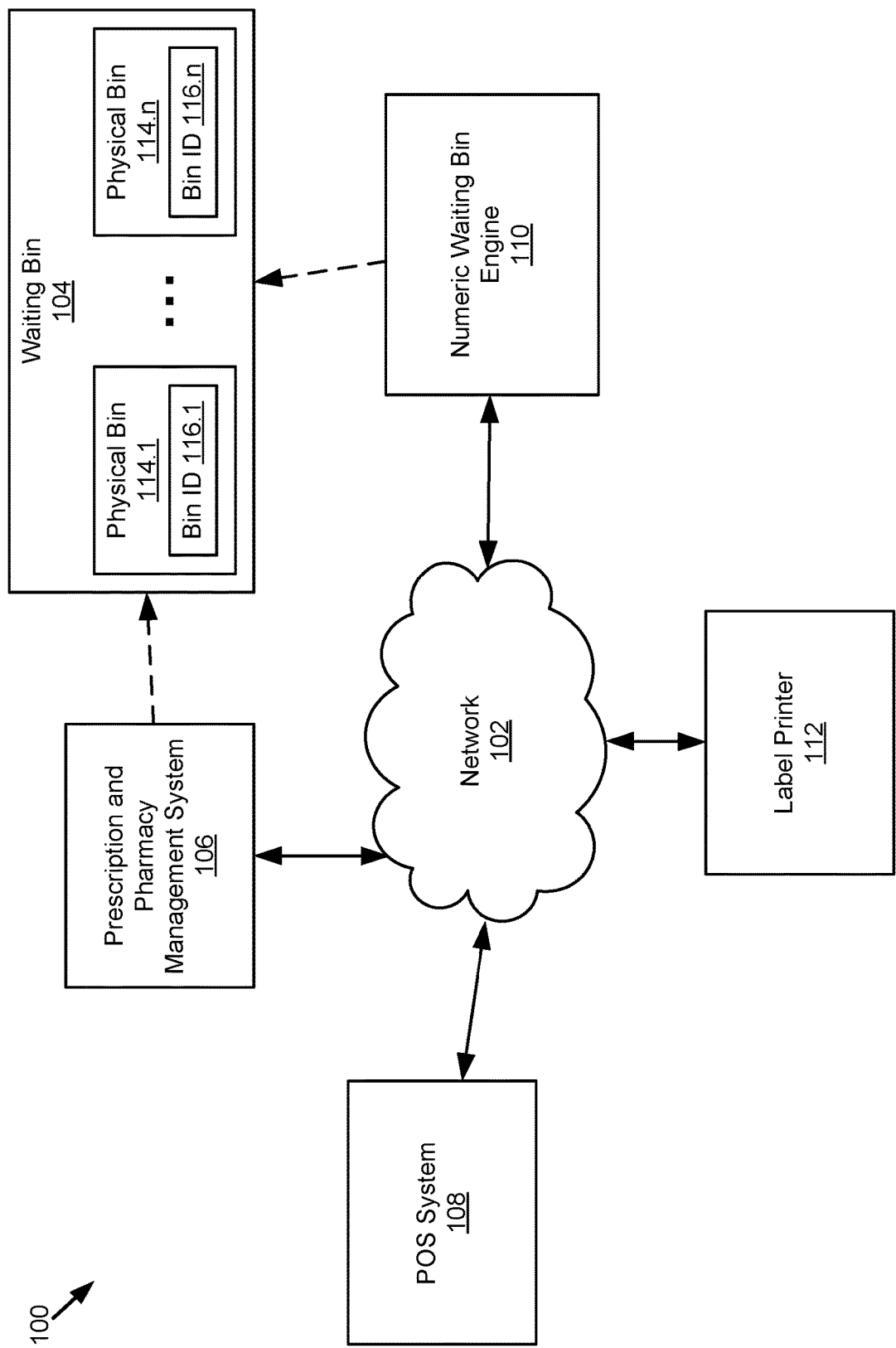
FIG. 1 is a block diagram of an example system for a numeric waiting bin for medication prescription fulfillment.

FIG. 1 is a block diagram of an example system 100 for medication prescription fulfillment. The illustrated system 100 may include a network 102, a waiting bin 104, a prescription and pharmacy management system 106, an POS system 108, a numeric waiting bin engine 110, and a label printer 112. Prescription and pharmacy management system 106, point-of-sale (POS) system 108, numeric waiting bin engine 110, and label printer 112 are electronically communicatively coupled to each other by the network 102 for interaction, communication and cooperation. Prescription and pharmacy management system 106, point-of-sale (POS) system 108, numeric waiting bin engine 110, and label printer 112 may each be independent computing systems in network communication over network 102 and/or may be components of a larger computing system, such as an enterprise pharmacy computing environment. In some embodiments, a single computing device may host or embody a user interface to prescription and pharmacy management system 106, point-of-sale (POS) system 108, numeric waiting bin engine 110, and/or label printer 112 and a plurality of such devices may be provided for a retail pharmacy containing waiting bin 104. It should be understood that FIG. 1 is just one implementation, and there may be other system configurations are possible including connection, communication and cooperation with other devices, systems, and networks.

Network 102 may include any number of networks and/or network types. For example, network 102 may include, but is not limited to, one or more local area networks (LANs), wide area networks (WANs) (e.g., the Internet), virtual private networks (VPNs), wireless wide area network (WWANs), WiMAX® networks, personal area networks (PANs) (e.g., Bluetooth® communication networks), various combinations thereof, etc. These private and/or public networks may have any number of configurations and/or topologies, and data may be transmitted via the networks using a variety of different communication protocols including, for example, various Internet layer, transport layer, or application layer protocols. For example, data may be transmitted via the networks using TCP/IP, UDP, TCP, HTTP, HTTPS, DASH, RTSP, RTP, RTCP, VOIP, FTP, WS, WAP, SMS, MMS, XMS, IMAP, SMTP, POP, WebDAV, or other known protocols.

Waiting bin 140 may include any configuration of physical storage for containing and organizing prescriptions ready for pickup. For example, a pharmacy may have one or more shelves and/or counter space designated for prescription storage for pickup. In some embodiments, a plurality of physical bins 114.1-114.n may be arranged along one or more shelves or counters that include walls, dividers, or similar barriers for separating one bin from the adjacent bins. For example, physical bins 114 may each be a rectangular plastic bin or tray with dimensions sized for accommodating the most common prescription packaging. In some configurations, drawers or other opening and/or moving receptacles may be used. Each physical bin 114 may receive a corresponding bin identifier 116.1-116.n from numeric waiting bin engine 110. For example, each physical bin 114 may be assigned a serial bin identifier, such as a numeric series, that are printed, written, displayed, or otherwise associated with each physical bin 114 as bin identifier 116.

Prescription and pharmacy management system 106 may include one or more computing devices having data processing and communication capabilities. For example, prescription and pharmacy management system 106 may include an enterprise pharmacy data system accessible through a plurality of computing terminals in the retail pharmacies. In some embodiments, prescription and pharmacy management system 106 may provide an interface and workflow for pharmacy staff to view and process prescriptions, such as within a retail pharmacy. Prescription and pharmacy management system 106 may receive prescriptions from prescribers electronically and may also allow prescriptions to be input manually by the pharmacist or pharmacy staff. Prescription and pharmacy management system 106 may also receive information from and send information to electronic medical records, insurance carriers and other systems. In some embodiments, prescription and pharmacy management system 106 may provide access to one or more pharmacy data warehouses and associated applications. For example, pharmacy users may access patient and prescription records for prescriptions being processed and/or fulfilled through their store. Prescription and pharmacy management system 106 may also track inventory, manager operations and tasks by the pharmacist or pharmacy staff, etc. As noted above, prescription and pharmacy management system 106 may be coupled for communication and cooperation with POS system 108, numeric waiting bin engine 110, and label printer 112. The functionality, structure, and operation of the prescription and pharmacy management system 106, particularly for cooperation with the waiting bin engine 110, is described in more detail below.

POS system 108 includes one or more computing devices having data processing and communication capabilities. In some embodiments, POS system 108 authorizes payment for patient prescriptions and can provide prior authorization for a prescription. POS system 108 is used to determine the amount owed by a customer and may include additional devices such as barcode scanners and cash registers. POS system 108 may include additional functionality, such as inventory management, CRM, financials or warehousing, etc. POS system 108 may be coupled to the systems of insurance payors for customers and systems of different financial and payment card companies. In some embodiments, POS 108 may provide a graphical user interface for accessing one or more functions of prescription and pharmacy management system 106. POS system 108 may be coupled for communication and cooperation with prescription and pharmacy management system 106, numeric waiting bin engine 110, and/or label printer 112. The functionality, structure, and operation of the POS system 108, particularly for cooperation with the waiting bin engine 110, is described in more detail below.

Numeric waiting bin engine 110 includes one or more computing devices having data processing and communication capabilities. Numeric waiting bin engine 110 may include one or more functional modules accessible through or integrated with POS system 108 and prescription and pharmacy management system 106. Numeric waiting bin engine 110 may integrate with one or more computerized workflows for managing prescription fulfillment and pickup using prescription and pharmacy management system 106 and the POS system 108. Numeric waiting bin engine 110 may systematically assign prescriptions a slot number, or similar unique serial identifier, corresponding to a physical bin in waiting bin 104 and effectively manage the number of prescriptions in each slot. In some embodiments, numeric waiting bin engine 110 may enable the assigned slot number for a selected prescription to be stored in a prescription record in prescription and pharmacy management system 106, printed by label printer 112 for attachment to the dispensed medication, and/or displayed on the graphical user interface of POS system 108 to increase retrieval efficiency. The functionality, structure, and operation of the numeric waiting bin engine 110 is described in more detail below.

Figure 2:
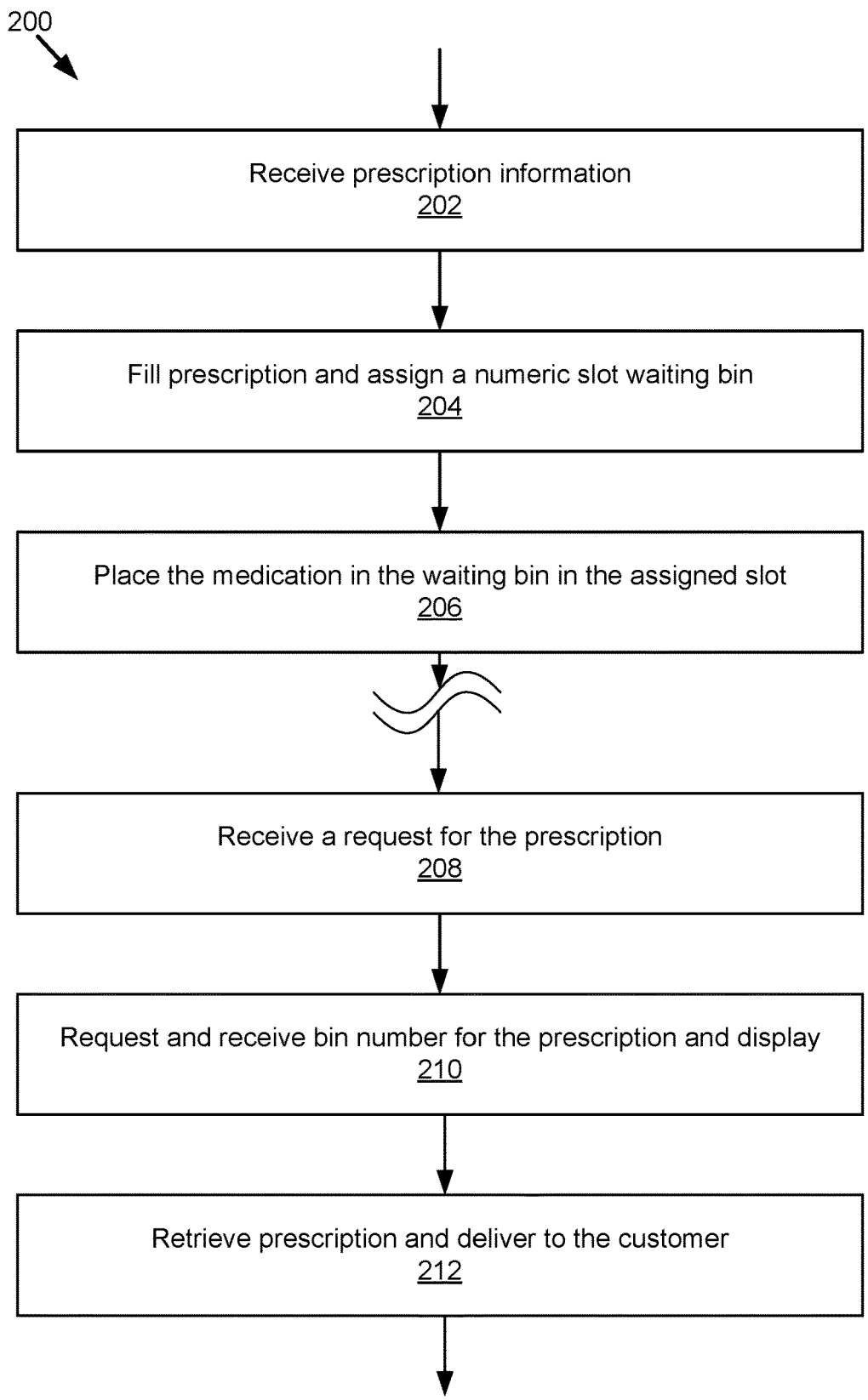
FIG. 2 is a flowchart of an example method for medication prescription fulfillment using a numeric waiting bin.

FIG. 2 is a flowchart of an example method 200 for medication prescription fulfillment using the numeric waiting bin. For example, method 200 may be executed using system 100 in FIG. 1. At 202, the system 100 receives prescription information. For example, prescription and pharmacy management system 106 may receive electronic prescription information from a prescriber, e.g., a physician, via the network 102.

At 204, prescription and pharmacy management system 106 controls filling the prescription and cooperates with the numeric waiting bin engine 110 to assign a slot for the prescription once the prescription is filled. For example, prescription and pharmacy management system 106 may provide a workflow to one or more pharmacists and/or pharmacy technicians for verifying the prescription and dispensing the medication into an appropriately labeled prescription container, including printing the label on label printer 112. Numeric waiting bin engine 110 may execute assignment of the slot and adding the slot serial identifier to the prescription information stored in prescription and pharmacy management system 106 and printed by label printer 112 as part of the workflow without otherwise requiring intervention by the user. At 206, the pharmacy staff then places the prescription in waiting bin 104 in the number slot assigned by numeric waiting bin engine 110. For example, using the slot number printed on the prescription label, the staff person matches the printed slot number to the slot number assigned to the physical bin and places the prescription in the physical bin for later pickup by the patient.

At a later time, the patient may request her prescription when she arrives at the pharmacy. At 208, POS system 108 may receive patient and/or prescription identifying information in a request for the prescription. For example, the pharmacy staff may interface with POS system 108 to retrieve the prescription record and pay for the prescription. At 210, numeric waiting bin engine 110 cooperates with POS system 108 to retrieve the slot number that indicates the physical bin location of the prescription. For example, this information may be displayed by POS system 108 for the pharmacy staff. At 212, the pharmacy staff retrieves the prescription from the indicated slot in waiting bin 104 and delivers it to the customer/patient.

In some embodiments, one or more actions in the pickup process may be integrated into one or more mobile applications available to a patient. For example, the patient may be able to use a mobile application to indicate that they are requesting the prescription and send the request received at 208. In some embodiments, a location-based service in the mobile device may indicate or prompt a pickup request automatically based on proximity to a pharmacy location. In some embodiments, at 212, the prescription may be retrieved and placed in a pickup location for delivery to the patient, such as a delivery areas adjacent a POS system or a self-service delivery unit. For example, a waiting bin engine may enable reassignment to such pickup areas in response to mobile/handheld technology providing a specific request type or following preconfigured pickup options for a particular patient, patient group, and/or prescription(s).

Figure 3:
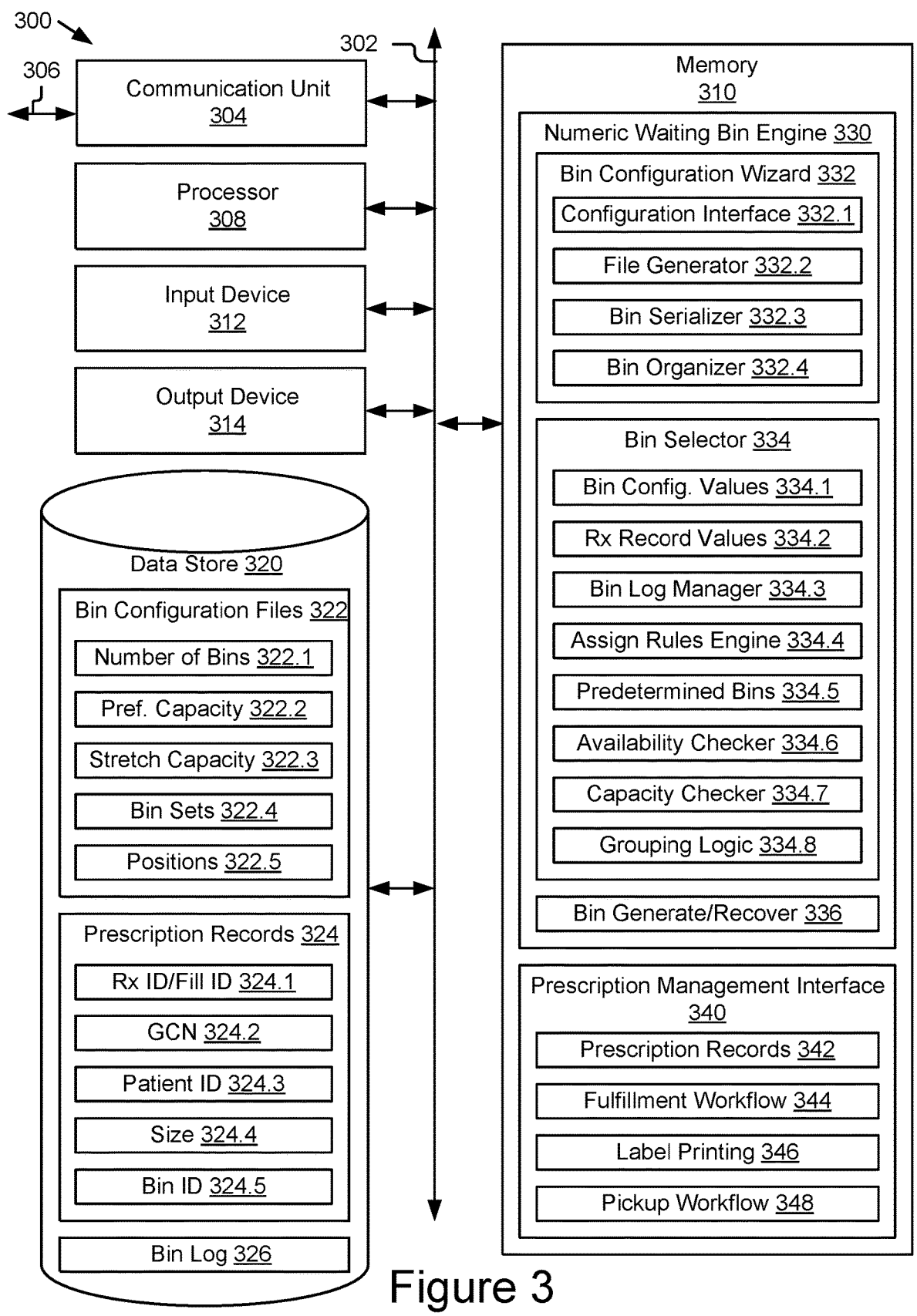
FIG. 3 is a block diagram of an example computing system.

FIG. 3 is a block diagram of an example computing device 300, which may represent a computing device configured to implement modules depicted in FIG. 1, depending on the implementation. In some embodiments, a plurality of computing devices 300 may contribute to an aggregate computing system that includes the components of computing device 300.

As depicted, the computing device 300 may include a processor 308, a memory 310, a communication unit 304, an output device 314, an input device 312, and a data store 320, which may be communicatively coupled by a communication bus 302. Computing device 300 depicted in FIG. 3 is provided by way of example and it should be understood that it may take other forms and include additional or fewer components without departing from the scope of the present disclosure. For instance, various components of the computing device may be coupled for communication using a variety of communication protocols and/or technologies including, for instance, communication buses, software communication mechanisms, computer networks, etc. While not shown, computing device 300 may include various operating systems, sensors, additional processors, peripheral devices (e.g. label printer 112), and other physical configurations. Processor 308, memory 310, communication unit 304, etc., are representative of one or more of these components. In some embodiments, one or more components of computing device 300 may be accessible to computing device 300 via communication unit 304 and one or more network interfaces, such as network communication via network 102.

Processor 308 may execute software instructions by performing various input, logical, and/or mathematical operations. Processor 308 may have various computing architectures to manipulate data signals (e.g., CISC, RISC, etc.). Processor 308 may be physical and/or virtual, and may include a single core or plurality of processing units and/or cores. In some implementations, processor 308 may be coupled to memory 310 via bus 302 to access data and instructions therefrom and store data therein. Bus 302 may couple processor 308 to the other components of the computing device 300 including, for example, memory 310, communication unit 304, input device 312, output device 314, and data store 320.

Memory 310 may store and provide data access to the other components of computing device 300. Memory 310 may be included in a single memory device or a plurality of memory devices. In some implementations, memory 310 may store instructions and/or data that may be executed by the processor 308. For example, memory 310 may store instructions and data, including, for example, an operating system, hardware drivers, other software applications, databases, etc. which may implement the techniques described herein. Memory 310 may be coupled to bus 302 for communication with processor 308 and the other components of computing device 300.

Memory 310 may include a non-transitory computer-usable (e.g., readable, writeable, etc.) medium, which can be any non-transitory apparatus or device that can contain, store, communicate, propagate or transport instructions, data, computer programs, software, code, routines, etc., for processing by or in connection with processor 308. In some implementations, memory 310 may include one or more of volatile memory and non-volatile memory (e.g., RAM, ROM, hard disk, optical disk, etc.). It should be understood that memory 310 may be a single device or may include multiple types of devices and configurations.

Bus 302 can include a communication bus for transferring data between components of a computing device or between computing devices, a network bus system including network 102 or portions thereof, a processor mesh, a combination thereof, etc. In some implementations, various components operating on the computing device 300 (operating systems, device drivers, etc.) may cooperate and communicate via a communication mechanism included in or implemented in association with bus 302. The software communication mechanism can include and/or facilitate, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

Communication unit 304 may include one or more interface devices (I/F) for wired and wireless connectivity among the components of the system 100. For instance, the communication unit 304 may include, but is not limited to, various types of known connectivity and interface options. In some embodiments, communication unit 304 may include a network interface, such as a network adapter, for communicating via a wired and/or wireless network 102 with other computing resources, devices, or systems. Communication unit 304 may be coupled to the other components of computing device 300 via bus 302. Communication unit 304 can provide other connections to the network 102 and to other entities of system 100 using various standard communication protocols.

Input device 312 may include any device for inputting information into computing device 300. In some implementations, input device 312 may include one or more peripheral devices. For example, input device 312 may include a keyboard, a pointing device, microphone, an image/video capture device (e.g., camera), a touch-screen display integrated with the output device 314, etc. Output device 314 may be any device capable of outputting information from the computing device 300. The output device 314 may include one or more of a display (LCD, OLED, etc.), a printer, a haptic device, audio reproduction device, touch-screen display, a remote computing device, etc. In some implementations, output device 314 may include a display which may display electronic images and data output by a processor of the computing device 300 for presentation to a user, such as the processor 308 or another dedicated processor. For example, output device 314 may include a monitor or other display to provide a graphical user interface between a user, such as pharmacy staff, and computing device 300.

Data store 320 may include information sources for storing and providing access to data. In some implementations, data store 320 may store data associated with a database management system (DBMS) operable on the computing device 300. For example, the DBMS could include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations.

The data stored by data store 320 may be organized and queried using various criteria including any type of data stored by them. Data store 320 may include data tables, databases, data files, data objects, or other organized collections of data.

Data store 320 may be included in computing device 300 or in another computing system and/or storage system distinct from but coupled to or accessible by computing device 300. Data stores 320 can include one or more non-transitory computer-readable mediums for storing the data. In some implementations, data stores 320 may be incorporated with memory 310 or may be distinct therefrom.

Components 304, 308, 310, 312, and/or 314 may be communicatively coupled by bus 302 and/or processor 308 to one another and/or the other components of computing device 300. In some implementations, components 304, 308, 310, 312, and/or 314 may include computer logic (e.g., software logic, hardware logic, etc.) executable by processor 308 to provide their acts and/or functionality. In any of the foregoing implementations, these components 304, 308, 310, 312, and/or 314 may be adapted for cooperation and communication with processor 308 and the other components of the computing device 300.

In the embodiment shown, memory 310 may instantiate and/or store numeric waiting bin engine 330 and prescription management interface 340 for execution by processor 308. For example, waiting bin engine 330 may manage: the configuration of a data structure, such as bin log 326, to organize serial identifiers and associated prescriptions for waiting bin 104; selection, assignment, and storage of slot serial identifiers for selected prescriptions; and the generation and recovery of available slots. Prescription management interface 340 may integrate the operation of waiting bin engine 330 into the prescription management process of a retail pharmacy and/or enterprise pharmacy computing system, such as prescription and pharmacy management system 106. For example, prescription management interface 340 may include interfaces to patient and prescription records, prescription fulfillment workflow and label printing, and pickup workflow, such as the pickup workflow of a retail pharmacy POS system for waiting bin 104. In some embodiments, prescription management interface 340 may be integrated into waiting bin engine 330 and/or they may be managed as separate libraries and/or background processes (e.g. daemon) through an API or other interface.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

Numeric waiting bin engine 330 may include an interface protocol or set of functions and parameters for configuring, assigning, and managing numeric waiting bin assignments for prescriptions awaiting pickup. In some embodiments, waiting bin engine 330 may include a plurality of hardware and/or software modules configured to use processor 306 and memory 310 to execute and manage defined operations of waiting bin engine 330. For example, waiting bin engine 330 may include a bin configuration wizard 332, a bin selector 334, and a bin generate/recover module 336. For any give pharmacy location and corresponding physical waiting bin configuration, waiting bin engine 330 may use bin configuration wizard 332 to receive bin configuration values, assign serial identifiers, and generate bin log 326 or a similar data structure for managing slot assignments. As prescriptions are fulfilled, waiting bin engine 330 may use bin selector 334 to select and assign slot serial identifiers to one or more prescriptions to be placed in those slots. As prescriptions are picked up, new prescriptions are fulfilled, and/or as a separate initialization and/or cleanup process, waiting bin engine 330 may use bin generate/recover module 336 to generate and/or identify available slots in waiting bin 104.

Bin configuration wizard 332 may include an interface and/or communication event-based condition for receiving bin configuration values from a user or other system utility and using them to generate a serial identifier model, such as an ordered series of number values for the corresponding physical waiting bins, and corresponding data structure. For example, bin configuration wizard 332 may be initiated through a pharmacy computing device as an administrative function of a prescription management system. In some embodiments, bin configuration wizard 332 may be an application or application component launched from an icon or menu in a graphical user interface of the prescription management system. For example, a system administrator or pharmacy manager may initiate bin configuration wizard 332 when numeric waiting bin engine 330 is first installed or enabled for their store and/or any time the configuration of physical waiting bins changes. In some instances, bin configuration wizard 332 may also be launched in order to modify one or more bin configuration values, such as preferred capacity or stretch capacity, based on changes in user preferences and/or prescription packaging or sizes. In some embodiments, bin configuration wizard 332 may be comprised of a plurality of submodules, functions, or subroutines for executing specific aspects of bin configuration wizard 332's functions. For example, bin configuration wizard 332 may include a configuration interface 332.1, a file generator 332.2, a bin serializer 332.3, and a bin organizer 332.4.

Configuration interface 332.1 may define a user interface and/or API for receiving bin configuration values, such as a set of bin configuration parameters used to model the physical waiting bins in a bin configuration data structure. For example, configuration interface 332.1 may define a graphical user interface comprised of one or more forms for receiving structured data from a user. In some embodiments, configuration interface 332.1 may include a plurality of fields for receiving bin configuration values and may generally correlate to the data structure of a bin configuration file 322 that may be used to store those values. For example, bin configuration wizard 332 may support bin configuration file 322 in data store 320 for storing bin configuration values in non-volatile storage. Configuration interface 332.1 may present one or more windows, pages, tabs, or similar graphical elements that contain labels and fields corresponding to number of bins 322.1, preferred capacity 322.2, and stretch capacity 322.3. In some embodiments, configuration interface 332.1 may include further interface options for managing multiple bin configuration sets to support bins of different sizes in the same waiting bin and/or enable position information for two-dimensional arrays of bins and other spatial arrangements. Configuration interface 332.1. may also provide options for loading, editing, saving, and resetting bin configuration values from an existing bin configuration file 322. In some embodiments, an API for receiving and modifying bin configuration values without invoking a graphical user interface may be provided by configuration interface 332.1. In some embodiments, the functions of bin configuration wizard 332, including configuration interface 332.1, may be executed through command line, general file or database editors, and/or similar general-purpose interfaces.

File generator 332.2 may include logic, interface protocols, and/or a set of functions and parameters for generating a file, database entry, or similar data structure for storing bin configuration values in non-volatile storage. For example, file generator 332.2 may use the bin configuration values received through configuration interface 332.1 to generate bin configuration file 322 in data store 320. In some embodiments, bin configuration file 322 may refer to a subset of a larger group of configuration parameters for a pharmacy that are stored in a store configuration file or similar data structure. File generator 332.1 may include an interface to data store 320 that transmits the bin configuration values and/or the bin configuration data structure from memory 310 to data store 320. In some embodiments, file generator 332.1 may further enable editing bin configuration file 322 responsive to additional bin configuration values received through configuration interface 332.1 and/or bin organizer 332.4. In some embodiments, file generator 332.2 may support configuration bin values sets 322.4 in one or more bin configuration files and/or include position values 322.5 for numeric waiting bin engines that support bin position information.

Bin serializer 332.3 may include logic, interface protocols, and/or a set of function and parameters for assigning unique serial identifiers to each physical bin determined from the bin configuration values. For example, configuration interface 332.1 may receive a number of bins value 322.1 and bin serializer 332.3 may generate an ordered series of unique identifiers equal to number of bins value 322.1. In some embodiments, bin serializer 332.3 may generate both a physical representation of the bin identifiers and a corresponding data structure or model of the bin identifiers. Each unique serial identifier may be placed on or otherwise associated with the physical bins in waiting bin 104, generally by pharmacy staff. In some embodiments, bin serializer 332.3 may display the range of serial identifiers or a list of serial identifiers through configuration interface 332.1. Bin serializer 332.3 may provide an interface for printing a plurality of bin identifier tags for attachment or display proximate the respective bins for reference by pharmacy staff when placing and picking up prescriptions. In some embodiments, bin serializer 332.3 may generate a data structure corresponding to the series of bin identifiers, such as bin log 326 instantiated in a bin log file stored in data store 320, that may be used by numeric waiting bin engine 330 to manage active slots containing prescriptions and generation of available slots when a new bin needs to be activated. For example, bin serializer 332.3 may generate a table, array, or similar data structure including the series of bin identifiers and one or more fields for identifying prescriptions and data related thereto for each bin identifier. This data structure may be stored as bin log 326 in data store 320.

Bin organizer 332.4 may include logic, interface protocols, and/or a set of functions and parameters for managing multiple sets of bin configurations and/or position information for more complex waiting bin models. For example, bin organizer 332.4 may enable configuration interface 332.1 to receive and organize multiple sets of bin configuration values and store them in bin sets 322.4. As another example, bin organizer 332.4 may enable configuration interface 332.1 to receive position information for bins or groups of bins, such as placing the bins in a two-dimensional array or grouped in different areas, that may impact the bin assignment rules used by bin selector 334. In some embodiments, bin organizer 332.4 may enable a user to customize the assignment of bin identifiers initially generated by bin serializer 332.3. For example, once bin serializer 332.3 has generated the serial identifiers and assigned them to the sequence of bins (with or without position information), bin organizer 332.4 may display and enable one or more options for reconfiguring and/or customizing the serial identifiers assigned to each bin, such as a drag and drop GUI for moving the identifies among bins or fields for customizing selected serial identifiers or bin assignments.

Bin selector 334 may include an interface and/or communication event-based condition for determining the slot assignments of one or more prescriptions during fulfillment. For example, during a prescription fulfillment workflow using a prescription management system, a prescription may be selected for fulfillment based on a user selection or an automated task queue. Within the work flow, one or more steps may indicate that the prescription has been prepared and is ready to be labeled and placed in a waiting bin for pickup. In some embodiments, a prescription filled or ready to be filled may trigger a call to numeric waiting bin engine 330 to select a physical waiting bin slot to receive the completed prescription. For example, fulfillment workflow interface 344 may issue a call or similar message to an API for numeric waiting bin engine 330 requesting a waiting bin slot for the selected prescription. Numeric waiting bin engine 330 may identify the bin selection request from the received call and pass the relevant parameters to bin selector 334. In some embodiments, bin selector 334 may be comprised of a plurality of submodules, functions, or subroutines for executing specific aspects of bin selector 334's functions. For example, bin selector 334 may include bin configuration values 334.1, prescription record values 334.2, bin log manager 334.3, assignment rules engine 334.4, predetermined bins lookup 334.5, availability checker 334.6, capacity checker 334.7, and/or grouping logic 334.8.

In some embodiments, the output of bin selector 334 is one or more bin identifier assignments for selected prescription(s). For example, bin selector 334 may generate bin identifier for a selected prescription and return the bin identifier and prescription identifier to numeric waiting bin engine 330. In some embodiments, bin selector 334 and/or numeric waiting bin engine 330 may store the selected bin identifier in bin identifier field 324.5 in prescription record 324 for the patient, prescription, and/or fill number. In some embodiments, assigned bin identifier may be displayed or printed on output device 314, such as a computing system or POS system display or a label printer for reference by pharmacy staff.

Bin configuration values 334.1 may include logic, interface protocols, and/or a set of functions and parameters for accessing bin configuration values and/or a bin configuration model based on bin configuration values for use by bin selector 334 in selecting and assigning a bin slot to a selected prescription. For example, bin configuration values 334.1 may include an interface protocol for reading values from bin configuration file 322 and storing the relevant values in a data structure in memory 310 for use by bin selector 334.

Prescription record values 334.2 may include logic, interface protocols, and/or a set of functions and parameters for accessing prescription record values, directly from prescription and/or related patient records and/or as parameters received by numeric waiting bin engine 330 as part of a bin selection request, for use by bin selector 334 in selecting and assigning a bin slot to a selected prescription. For example, prescription record values 334.2 may include an interface protocol for reading values from prescription record 324 and storing the relevant values in a data structure in memory 310 for use by bin selector 334.

In some embodiments, bin selector 334 may receive or access a plurality of prescription data values, such as a prescription identifier and/or fill identifier 324.1, a generic code number (GCN) 324.2, a patient identifier 324.3, and/or a prescription size value 324.4. For example, a prescription manage system may use a unique prescription identifier to manage each prescription in the system and a fill identifier for each individual fill of that prescription, and these values may be stored in one or more fields for prescription identifier and/or fill identifier 324.1. Each prescription may have GCN 324.2 that identifies the specific drug or pharmaceutical in the prescription and may designate associated dosing, form, and/or special handling relevant to that drug. While GCN refers to one drug classification system, other drug classification identifiers, such as generic product identifier (GPI) or American Hospital Formulary System (AHFS) identifiers may be used similarly, as could other drug classification systems, including proprietary systems. Each prescription may have an associated patient identifier 324.3 that designated the patient or customer the prescription is for. A patient identifier may include patient name, a unique combination of personally identifiable information, and/or a unique patient identifier assigned by the system or from another source, such as a social security number. In some embodiments, patient identifier 324.3 may enable access to patient records with additional information about the patient that may be relevant to prescription fulfillment and selecting and assigning bin slots. For example, patient identifier 324.3 may be used to access grouping information, such as multiple prescriptions for a household that are likely to be picked up together, or other pickup preferences. Prescription size value 324.4 may include one or more values describing the estimated size of the resulting prescription and related packaging. In some embodiments, prescription size value 324.4 may include specific pill size and count, volumes of fluid prescriptions, and/or specific package sizes, such as standard dram vials or prescription bottles, blister packs, etc. In some embodiments, sizes values may be standardized around a more general sizing approach, such as a standard size (that may have a null value for size) and oversize, or an abstract size range and increments (e.g. 1-5 based on how many physical bin slots the packaged prescription is expected to fill). In some embodiments, prescriptions that are not oversized may be given a standard size (1 unit) and a number of prescriptions or prescription count may be used for managing bin capacity and assignments.

Bin log manager 334.3 may include logic, interface protocols, and/or a set of functions and parameters for accessing and changing current bin slot assignment information, such as bin log 326, for use by bin selector 334 in selecting and assigning a bin slot to a selected prescription. For example, bin log manager 334.3 may include an interface protocol for reading values from and/or writing values to bin log 326 and storing the relevant values in a data structure in memory 310 for use by bin selector 334.

Assignment rules engine 334.4 may include logic, interface protocols, and/or a set of functions and parameters for determining bin slot assignments for each prescription processed and use by bin selector 334 in selecting and assigning a bin slot to a selected prescription. For example, assignment rules engine 334.4 may include a logic engine that processes a plurality of logical rules from one or more rules definitions to evaluate parameters of bin configuration values 334.1, prescription record values 334.2, bin log 326, and/or other resources to determine bin slot assignments. In some embodiments, rules engine 334.4 may be implemented using a rules processor that steps through a plurality of logical evaluations to determine a bin slot, such as the process(es) described below with regard to FIGS. 4-8. Example classes of assignment rules may include: evaluating a predetermined bin list, checking the availability of partially allocated bins in the bin log (based on preferred and/or stretch capacity), checking total bin capacity and whether any unused bins are available for allocation, and grouping logic used to group related prescriptions for pickup and/or otherwise group prescriptions to improve waiting bin maintenance and pickup processing. Examples of these assignment rules may be provided below with regard to predetermined bins lookup 334.5 (predetermined assignment rules), availability checker 334.6 (bin/slot availability rules), capacity checker 334.7 (capacity checking rules), and grouping logic 334.8 (grouping logic rules). In some embodiments, assignment rules engine 334.4 may also implement rules for bin generation and recovery, such as described below for bin generate/recovery module 336.

Predetermined bins lookup 334.5 may include logic, interface protocols, and/or a set of functions and parameters for determining fixed bin slot assignments for defined types of prescriptions. For example, predetermined bins lookup 334.5 may include rules for evaluating one or more predetermined bin tables indexed by one or more prescription record values 334.2, such as GCN 324.2, patient ID 324.3, and/or size 324.4. In some embodiments, GCN 324.2 may be used as an index to various prescription classes that require special handling, categories such as refrigerate, reconstitute, immunization, controlled, and excluded. GCN 324.2 may enable a pharmacy to classify the type of prescription and determine whether the prescription can be allocated to the general waiting bins or needs to be directed to a special waiting bin or waiting area for a special handling category. For example, a GCN that corresponds to refrigerate would require that the bin slot assigned is within a refrigerator or a GCN that corresponds to controlled would require that the bin slot assigned is in a special handling area for highly controlled substances. Patient ID 324.3 may enable a pharmacy to capture special handling instructions on a per-patient basis. For example, a patient may be allowed to designate that specific types of prescriptions be placed in a special handling area or exempted from grouping rules. In some embodiments, the pharmacy may place patient specific assignments based on patterns of pickup behavior or known high-volume users. Size 324.4 and/or groupings of prescriptions may enable a pharmacy to identify oversized items that should not be allocated to the general pool of waiting bins and are instead placed in an oversized special handling area for pickup. For example, a bulk capacity value may set a threshold for allocating bins to an oversized area. In some embodiments, multiple size classes, including an oversized class, may be used to allocate prescriptions among differently sized bin sets. In some implementations, fixed bin slot assignments may use a special numeric or non-numeric identifier that corresponds to the special handing areas assigned, such as "OVERSIZED" or "REFRIGERATE".

Availability checker 334.6 may include logic, interface protocols, and/or a set of functions and parameters for determining the availability of existing bins and bin slots for additional prescriptions. For example, predetermined bins lookup 334.5 may include rules for determining whether any given bin in the bin log has available slots based on a series of evaluations to optimally place the prescription for pickup. In some embodiments, the serial nature of the bin identifiers may locate one terminal identifier in the series nearest the pickup counter and associated POS system and the other terminal identifier furthest from the pickup counter. In such an arrangement, preferentially filling the lower numbered bin slots reduces the distance that staff will need to travel to retrieve the prescription from the waiting bins. In some embodiments, availability checker 334.6 may implement one or more rules for allocating bin slots based on preferred capacity versus stretch capacity. For example, the rules may allocate to preferred capacity until all bins are at preferred capacity and no unused bins remain to be allocated. More complex rules for managing preferred capacity may interact with grouping logic 334.8, capacity checker 334.7, and other factors for managing the use of stretch capacity. In some embodiments, availability checker 334.6 may support allocation among multiple bin sets with different capacities and rules for managing allocation across those bin sets may also be included. In some embodiments, availability checker 334.6 may process groups of prescriptions and use number of prescriptions or prescription count for evaluating availability for the prescription group or set.

Capacity checker 334.7 may include logic, interface protocols, and/or a set of functions and parameters for managing total capacity of the waiting bins and determining the allocation of additional bins for additional prescriptions as needed. For example, capacity checker 334.5 may include rules for determining whether unused bins are available within the bin configuration and make those bins available for allocation by availability checker 334.6 when needed. In some embodiments, capacity checker 334.7 may make a next serial bin identifier available in response to a series of logical evaluations by availability checker 334.6 determine that no availability or no preferred availability is currently available in the allocated bin slots. For example, capacity checker 334.7 may enforce concentration of prescriptions into a limited set of bins until additional capacity is required. In some embodiments, capacity checker 334.7 may also include rules based on positions 322.5 and/or in sets 322.4 for determining what next bin identifier should be allocated for use by bin selector 334.

Grouping logic 334.8 may include logic, interface protocols, and/or a set of functions and parameters for grouping prescriptions in the waiting bins for easier location and pickup. For example, grouping logic 334.8 may include rules for determining whether multiple prescriptions belong to the same patient and/or a patient group that is generally picked up together (e.g. a family or other patient group). In some embodiments, grouping logic 334.8 may include rules for locating the bin assignments of related prescriptions, such as using patient ID or a related index of grouped patient IDs, determining whether a previously assigned bin slot for a related prescription has capacity for the new prescription, an adjacent slot has capacity for the new prescription, or both the new and prior prescriptions can be relocated to a bin slot that includes adequate capacity. For example, for each new prescription, grouping logic 334.8 may identify each related prescription (such as each prescription for the same patient) and process them as a batch for bin assignment or may include rules for selectively relocating one or more prescriptions. In some embodiments, grouping logic 334.8 may access all active prescriptions waiting to be filled in the system, not just those that have been fulfilled, for determining grouping assignments. In some embodiments, grouping logic 334.8 may pre-assign one or more slots to pending prescriptions and allocate them in bin log 326, whereby the pending prescription will automatically be assigned the pre-assigned slot when the prescription is filled.

In some embodiments, bin selector 334 may enable a manual override of bin assignments. For example, assignment rules engine 334.4 may automatically generate a bin assignment for one or more prescriptions and display the assignment to a user, but provide an override option, such as a menu, button, or editable field to allow the user to input or otherwise manually identify an override bin assignment. Numeric waiting bin engine 330 may validate the selection to assure that it does not conflict with prior waiting bin assignments, then treat the manually entered bin identifier similarly to those automatically generated by bin selector 334. In some embodiments, manually selected bin assignments may also generate a flag or other identifier that may be stored with bin identifier 324.5 to indicate that the bin assignment was manually selected rather than system generated. This may enable system administrators to monitor use of manual overrides.

Bin generate/recover module 336 may include logic, interface protocols, and/or a set of functions and parameters for generating and recovering empty waiting bins, bin slots, and/or bin identifiers. For example, bin generate/recover module 336 may include rules for bin generation and bin recovery. In some embodiments, bin generation rules and bun recovery rules may be executed by assignment rules engine 334.4 and/or a common rules engine accessible to both bin selector 334 and bin generate/recover module 336. Bin generation rules may provide logic for identifying one or more available bins within capacity. In some embodiments, bin generation rules may interact with capacity checker 334.7 of bin selector 334. In some embodiments, bin generate/recover module 336 may implement the process(es) of FIG. 5 below. Bin recovery rules may provide logic for recovering bin slots after prescriptions have been picked up or otherwise removed from waiting bins. In some embodiments, bin recovery rules may interact with availability checker 334.6 for identifying available bin slots and bin identifiers. In some embodiments, bin generate/recover module 336 may operate in conjunction with pickup workflow interface 348 and bin log manager 334.3 to assure that capacity made available by picked up or otherwise disposed of prescriptions is reflected in bin log 326 and recovered for use by availability checker 334.6.

Prescription management interface 340 may include an interface protocol or set of functions and parameters for accessing one or more prescription and pharmacy management systems in support of the functions of numeric waiting bin engine 330. In some embodiments, prescription management interface 340 may include a plurality of hardware and/or software modules configured to use processor 306 and memory 310 to execute and manage defined operations of prescription management interface 340. For example, prescription management interface 340 may include a prescription records interface 342, a fulfillment workflow interface 344, a label printing interface 346, and a pickup workflow interface 348. In some embodiments, each of these interfaces may include applications, APIs, and/or functions to access resources in an enterprise pharmacy computing environment comprised of one or more data systems or subsystems, such as those shown in FIG. 1. In some embodiments, one or more of these prescription management functions may be directly integrated with numeric waiting bin engine 330 and/or data store 320 and the interfaces shown may include local function calls or similar interactions within an integrated application environment on one or more computing systems.

Prescription records interface 342 may include logic, interface protocols, and/or a set of functions and parameters for accessing prescription records 324. For example, prescription records interface 342 may include an API and messaging protocol for querying prescription records 324 for prescription/fill identifiers 324.1, GCN 324.2, patient identifier 324.3, size 324.4, bin identifier 324.5, and other prescription and patient record fields or related data structures. In some embodiments, prescription records interface 342 may include an API for writing one or more values related to numeric waiting bin engine 330 to patient and/or prescription records. For example, an assigned bin ID 324.5 may be stored in prescription records 324 and be accessible through one or more prescription and/or pharmacy management systems to allow pharmacy staff to access bin assignments outside of a specific workflow, such as a fulfillment workflow or pickup workflow. One or more pharmacy information systems may allow pharmacy staff to look up bin identifiers for active prescriptions from a patient information screen, through a bin assignment search function, and/or as part of backend inventory management, return-to-stock procedures, or other aggregate processes for managing waiting bin contents. In some embodiments, bin identifiers 324.5 may be accessed from prescription records 324 and/or maintained in a separate storage location for enabling aggregate workflows for managing the waiting bins. For example, a return-to-stock report, such as a day 14 report, may be sorted by bin identifier to enable pharmacy staff to move sequentially through the waiting bins to pull prescriptions to be returned to stock.

Fulfillment workflow interface 344 may include logic, interface protocols, and/or a set of functions and parameters for integrating a prescription fulfillment workflow with numeric waiting bin engine 330. For example, fulfillment workflow interface 344 may include an API and messaging protocol for receiving requests for bin identifier assignments and providing response messages during execution of prescription fulfillment workflow on one or more pharmacy and/or enterprise computing systems. In some embodiments, one or more steps in a prescription fulfillment workflow may trigger a request to numeric waiting bin engine 330 through fulfillment workflow interface 344. For example, when a prescription is verified for fill or a fill is complete, a new bin identifier may be requested in order to print the bin identifier on the prescription label, display the bin identifier to the staff for placing the prescription, and/or storing the bin identifier in the prescription records for later reference by other systems.

Label printing interface 346 may include logic, interface protocols, and/or a set of functions and parameters for integrating the label printing and/or document generation processes within a pharmacy with numeric waiting bin engine 330. For example, when a prescription is filled, a label may printed for the container with the prescribed drugs and additional instructions, warnings, and other documentation are printed for use by the patient and pharmacy staff and label printing interface 346 may receive or retrieve a bin identifier for the prescription from numeric waiting bin engine 330. In some embodiments, label printing interface 346 may be configured to communicate with numeric waiting bin engine 330 to receive the bin identifier for the selected prescription. In some embodiments, label printing interface 346 may receive the bin identifier from prescription records 324 or the prescription fulfillment workflow accessed by fulfillment workflow interface 344. Label printing interface 346 may include location and formatting information defining how the bin identifier is configured on the printed label and/or other documentation.

Pickup workflow interface 348 may include logic, interface protocols, and/or a set of functions and parameters for integrating a prescription pickup workflow with numeric waiting bin engine 330. For example, pickup workflow interface 348 may include an API and messaging protocol for receiving requests for bin identifier assignments and providing response messages during execution of prescription pickup workflow on one or more pharmacy computing systems, such as POS systems. In some embodiments, pickup workflow interface 348 may also communicate with numeric waiting bin engine 330 to update bin log 326 on prescriptions that have been picked up, thus freeing bin space. For example, when a pickup process is complete, the prescription identifier for the picked up prescription(s) may be communicated to numeric waiting bin engine 330 and bin log manager 334.3 may remove the prescription identifier and bin identifier assignment from bin log 326. In some embodiments, the pickup workflow may directly remove the bin identifier assigned from prescription records 324 or the no longer valid bin identifier may remain as part of the fill and transaction record (but not otherwise apply to current or future fills of that prescription).

Note that the interfaces between numeric waiting bin engine 330 and the workflow processes and other systems may be highly dependent on the configuration of those systems. Each pharmacy may have different prescription record, prescription fulfillment, label printing, and pickup workflow configurations and prescription management interface 340 may be configured to interact with whatever systems are available without substantially changing the function of numeric waiting bin engine 330.

In some embodiments, numeric waiting bin engine 330 and/or the related data in data store 320 may be used to further improve or automate pharmacy operations. For example, other waiting bin management tasks or workflows may be improved based on dynamic waiting bin assignments, such as enabling waiting bin inventory and/or revenue recognition to be performed automatically without manual scanning (or scanning only by exception). Individual pharmacy and/or enterprise-level analysis of waiting bin usage based on the data from numeric waiting bin engine 330 may enable assessment of physical layouts and space needs, including configuration of physical bins (number, size, and/or location) and special handling areas/bins, such as refrigerator space.

Figure 4A:
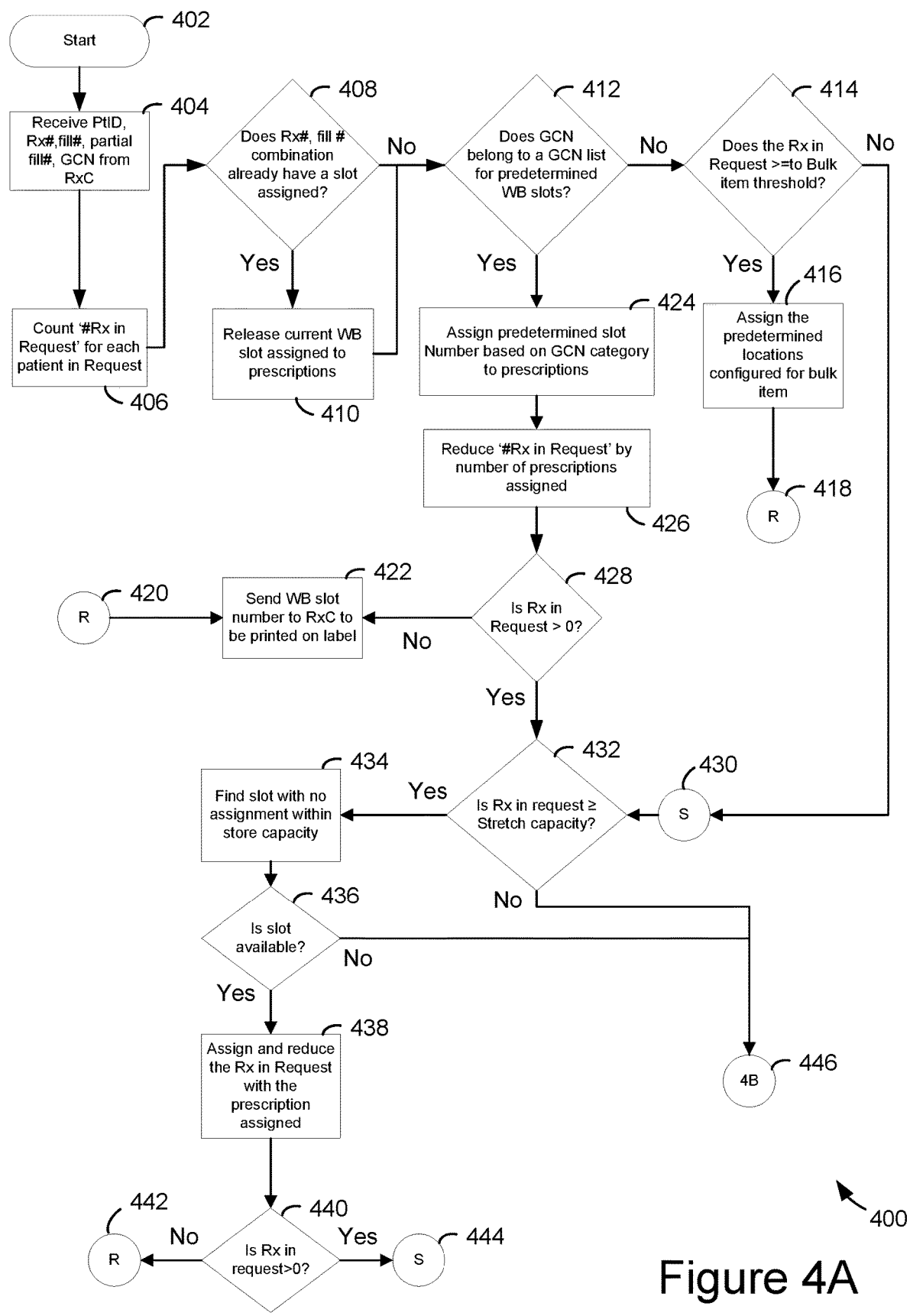
FIGS. 4A-4C are a flowchart of an example method for processing medication prescriptions using a waiting bin engine.
Figure 4B:
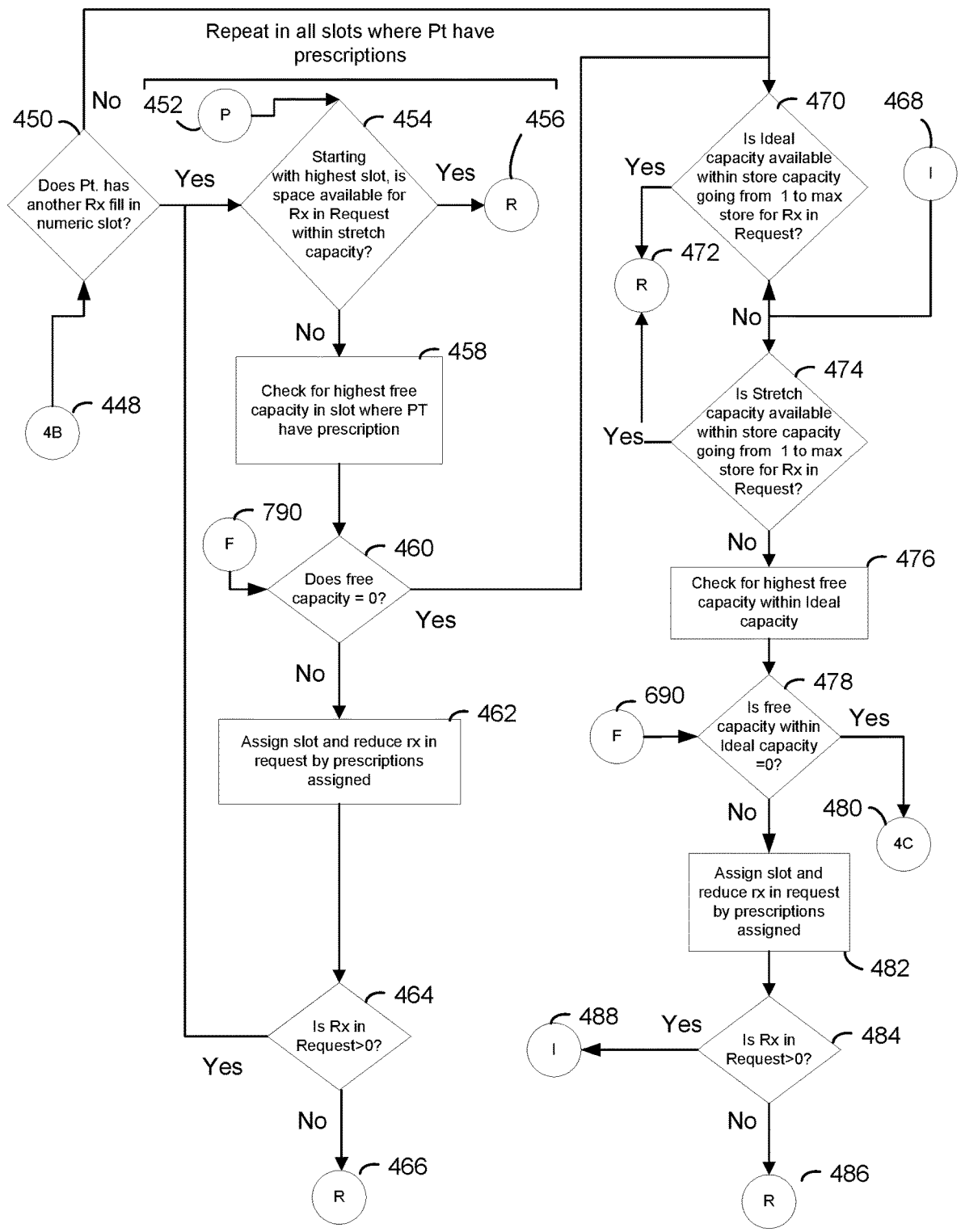
Figure 4C:
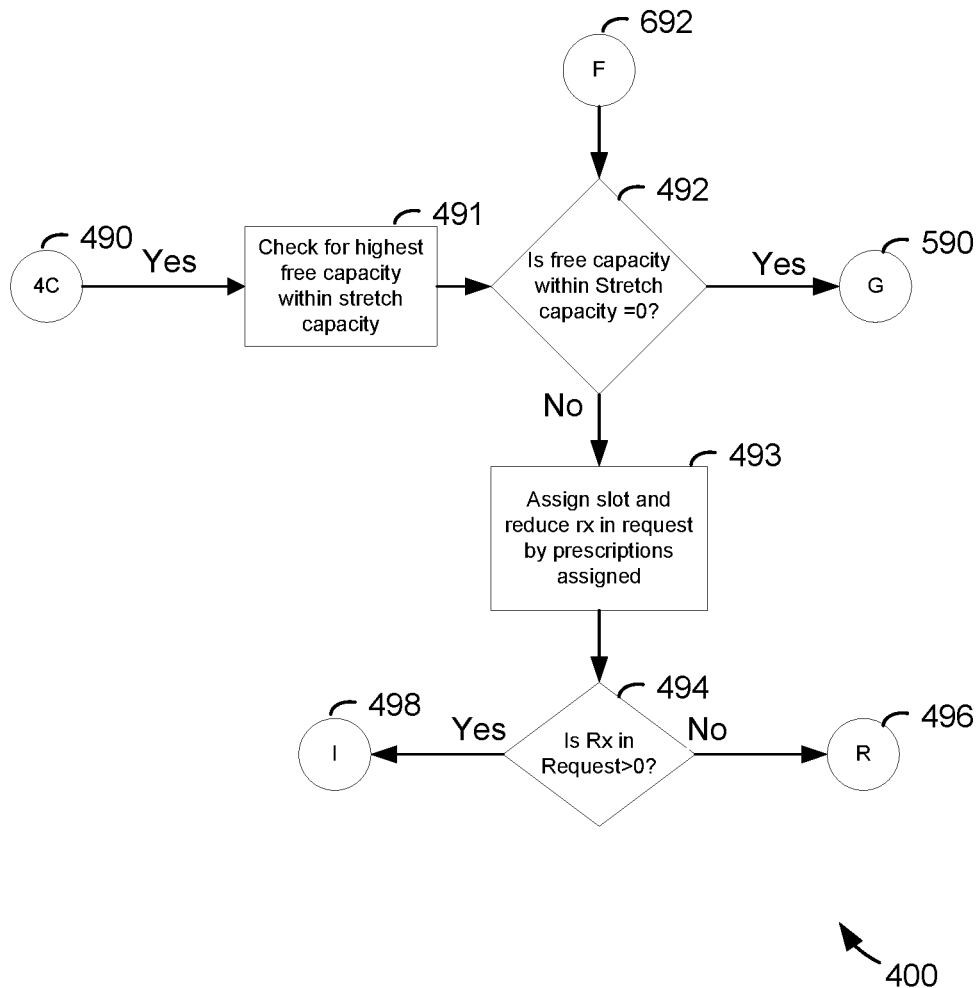

FIG. 4, including FIGS. 4A, 4B, and 4C, describes an example method 400 of selecting a bin identifier for a prescription in a prescription request, such as the prescription requests processed through a prescription fulfillment workflow. In some embodiments, method 400 may be executed by a waiting bin engine, such as numeric waiting bin engine 330 in FIG. 3. Computer-based method steps may be executed by one or more computing systems, such as computing device 300 and/or one or more of the components of system 100. In some embodiments, the blocks of method 400 may correspond to assignment rules evaluated by a rules engine in the computing system. "RxC" in the figures may refer to an example proprietary prescription and pharmacy management system and embodiments may not be limited to that system.

Method 400 may start at 402. At 404, prescription information may be received by the system. For example, a waiting bin engine may receive a request message including a patient identifier, a prescription identifier, a fill identifier, a partial fill identifier, and/or a GCN for a selected prescription. At 406, the number of prescriptions for each patient in the request may be counted. For example, the waiting bin engine may count the number of prescriptions by aggregating related fields for patients with one or more prescriptions in the request.

At 408, whether the prescription fill already has a slot assigned may be evaluated. For example, a combination of the prescription identifier and fill identifier may be compared against a bin log or an associated bin identifier field may be checked. If yes, the prescription fill already has a slot assigned, method 400 may proceed to 410 and release the current slots assigned to the prescriptions in the request. If no, the prescriptions do not have slot assignments, method 400 may proceed to 412. In some embodiments, 404-408 may be executed by At 412, whether the prescription fill has a GCN that correlates to a predetermined slot may be evaluated. For example, the GCN from the request may be used to index a table of predetermined waiting bin slots for special handling associated with the GCN. If yes, method 400 may proceed to 424. If no, method 400 may proceed to 414.

At 414, whether the number of prescriptions and/or size of a prescription or group of prescriptions in the order indicates bulk item handling may be evaluated. For example, the waiting bin engine may evaluate whether the number of prescriptions in the order exceeds or equals a configurable bulk threshold value or bulk capacity value. In some embodiments, a bulk size threshold value may be compared to a size value for a prescription or aggregate size values for a group of prescriptions to see if the bulk size threshold value has been exceeded. If no, the prescription does not indicate bulk item handling and method 400 may proceed to 430. If yes, method 400 may proceed to 416. At 416, a predetermined location configured for bulk items may be assigned to the prescription. For example, the waiting bin engine may assign a predetermined bin identifier associated with a bulk item storage location that may include one or more larger bins or similar holding area. Method 400 may proceed to 418, which corresponds to continuing method 400 from 420 to 422.

At 422, a waiting bin slot assignment for each selected prescription may be delivered to the requesting system. For example, the waiting bin engine may return a bin slot serial identifier or predetermined slot identifier to the requesting system to be displayed to a user, stored in a prescription record, and/or printed on the label and/or other packaging of each prescription. 422 may be an endpoint for method 400.

At 424, predetermined bin identifiers may be assigned to prescriptions. For example, the waiting bin engine may use the GCN category corresponding to predetermined bin slot numbers to assign one or more bin identifiers based on the GCN. At 426, the number of prescriptions in the request may be reduced by the number of prescriptions assigned at 424. For example, a request may contain three prescriptions for a patient, one of which receives special handling based on GCN, so the number of prescriptions remaining in the request after the predetermined slot is assigned may be two. At 428, the number of prescriptions in the request may be checked to determine whether additional prescriptions still need bin assignments. For example, in the example above, two prescriptions still remain after the predetermined bin assignment, so the number of prescriptions in the request is still greater than 0. If no, the number of prescriptions in request has reached zero and method 400 may proceed to 422 as described above. If yes, the number of prescriptions is greater than zero and method 400 may proceed to 432.

At 432, whether the remaining prescriptions in request exceed stretch capacity may be evaluated. For example, the waiting bin engine may compare the number of prescriptions in the request and their resultant size to the stretch capacity available in existing slots, such as slots that may contain another prescription for the same patient or group. If yes, the prescriptions are greater than the stretch capacity and method 400 may proceed to 434. If no, the prescriptions are less than the stretch capacity and method 400 may proceed via 446 and 448 to 450 in FIG. 4B.

At 434, store capacity may be searched for an available bin slot. For example, the waiting bin engine may check a bin log to determine whether there are slots with no assignment that are still within store capacity, such as number of bins in the waiting bins. At 436, the availability of unassigned slots may be evaluated. For example, a search at 434 may or may not yield an available slot within store capacity. If no, no slots are available and method 400 may proceed via 446 and 448 to 450 in FIG. 4B. If yes, a slot is available and method 400 may proceed to 438.

At 438, bin identifiers for the available slot may be assigned to prescriptions and the prescriptions in the request may be reduced. For example, the waiting bin engine may assign a next available slot identified at 434 to one or more prescriptions and the number of prescriptions in the request may be reduced by the number of prescriptions assigned. At 440, the number of prescriptions in the request may be checked to determine whether additional prescriptions still need bin assignments. If no, the number of prescriptions in request has reached zero and method 400 may proceed through 442 and 420 to 422 as described above. If yes, the number of prescriptions is greater than zero and method 400 may proceed through 444 and 430 to 432.

At 450 in FIG. 4B, whether the patient or other group has another prescription already assigned a waiting bin slot. For example, the patient identifier may be used by the waiting bin engine to search the bin log for other prescriptions awaiting pickup that have previously been assigned a slot serial identifier. If no, the patient or group does not have another prescription fill assigned and method 400 may proceed to 470. If yes, there may be one or more prescriptions with assigned slots and method 400 may proceed to 454.

At 454, each previously assigned bin slot may be evaluated to determine whether the new prescriptions are within stretch capacity for the previously assigned bin slot. For example, starting with the highest slot space the waiting bin engine may evaluate whether space is available for the prescriptions in the request based on the stretch capacity of the possible slots. If yes, the prescriptions are within the stretch capacity of a previously assigned bin slot for the patient and method 400 may proceed through 456 and 420 to 422 as described above. If no, the prescriptions are not within the stretch capacity of the previously assigned bin slot and method 400 may proceed to 458. 454 and resulting steps may be repeated for all slots with previously assigned prescriptions in the group. At 452, other steps may access or initiate 454.

At 458, among the previously assigned bin slots the highest free capacity may be checked. For example, if a patient or group has three previously assigned prescriptions with slot serial identifiers, each of those prescriptions may be checked to determine how much free capacity or availability remains in terms of size or number of prescriptions by comparing the number of prescriptions or aggregate size of prescriptions in each assigned bin to a capacity value for the bin configuration. At 460, the free capacity may be evaluated to determine whether it is zero. If yes, the highest free capacity is 0 and method 400 may proceed to 470. If no, there is free capacity and method 400 may proceed to 462.

At 462, bin identifiers for the available slot may be assigned to prescriptions and the prescriptions in the request may be reduced. For example, the waiting bin engine may assign the bin with the highest free capacity identified at 458 to one or more prescriptions and the number of prescriptions in the request may be reduced by the number of prescriptions assigned. At 464, the number of prescriptions in the request may be checked to determine whether additional prescriptions still need bin assignments. If no, the number of prescriptions in request has reached zero and method 400 may proceed through 466 and 420 to 422 as described above. If yes, the number of prescriptions is greater than zero and method 400 may proceed return to 454 to check the next highest slot with space available and a previously assigned prescription for the patient or group.

At 470, a preferred or ideal capacity may be evaluated for bins within the configuration. For example, available preferred capacity may be checked for each serial identifier in the bin log from a start value (e.g. 1) to a maximum value for the configuration (e.g. number of bins value) against the size or number of prescriptions in the request. If yes, there are bins with availability at their preferred capacity value and method 400 may proceed through 472 and 420 to 422 as described above. If no, there are no active bins with availability at their preferred capacity value and method 400 may proceed to 474.

At 474, a stretch capacity may be evaluated for bins within the configuration. For example, available stretch capacity may be checked for each serial identifier in the bin log from a start value (e.g. 1) to a maximum value for the configuration (e.g. number of bins value) against the size or number of prescriptions in the request. If yes, there are bins with availability at their stretch capacity value and method 400 may proceed through 472 and 420 to 422 as described above. If not, there are no active bins with availability at their stretch capacity value and method 400 may proceed to 476.

At 476, an available capacity within the preferred capacity may be checked for all active bins. For example, 474 may not have identified a single bin with available capacity for the prescriptions in the request, but there may still be bins with availability that could receive a portion of the prescriptions in the request, so the highest available or free capacity may be identified. At 478, the highest available or free capacity within the ideal or preferred capacity may be evaluated to determine whether it has reached zero (no remaining availability at the preferred capacity value). If no, free capacity is greater than 0 and method 400 may proceed to 482. If yes, no free capacity is available at the preferred values and method 400 may proceed through 480 and 490 to 491 in FIG. 4C.

At 482, bin identifiers for the available slot may be assigned to prescriptions and the prescriptions in the request may be reduced. For example, the waiting bin engine may assign the bin with highest available free capacity (greater than 0) identified at 476 to one or more prescriptions and the number of prescriptions in the request may be reduced by the number of prescriptions assigned. At 484, the number of prescriptions in the request may be checked to determine whether additional prescriptions still need bin assignments. If no, the number of prescriptions in request has reached zero and method 400 may proceed through 486 and 420 to 422 as described above. If yes, the number of prescriptions is greater than zero and method 400 may proceed through 488 and 468 to 470.

At 491 in FIG. 4C, an available capacity within the stretch capacity may be checked for all active bins. For example, 474 may not have identified a single bin with available capacity for the prescriptions in the request, but there may still be bins with availability that could receive a portion of the prescriptions in the request, so the highest available or free capacity may be identified. At 492, the highest available or free capacity within the stretch capacity may be evaluated to determine whether it has reached zero (no remaining availability at the stretch capacity value). If no, free capacity is greater than 0 and method 400 may proceed to 493. If yes, no free capacity is available at the stretch values and method 400 may proceed through 590 and 504 to method 500 in FIG. 5.

At 493, bin identifiers for the available slot may be assigned to prescriptions and the prescriptions in the request may be reduced. For example, the waiting bin engine may assign the bin with highest available free capacity (greater than 0) identified at 491 to one or more prescriptions and the number of prescriptions in the request may be reduced by the number of prescriptions assigned. At 494, the number of prescriptions in the request may be checked to determine whether additional prescriptions still need bin assignments. If no, the number of prescriptions in request has reached zero and method 400 may proceed through 496 and 420 to 422 as described above. If yes, the number of prescriptions is greater than zero and method 400 may proceed through 488 and 468 to 470.

Figure 5:
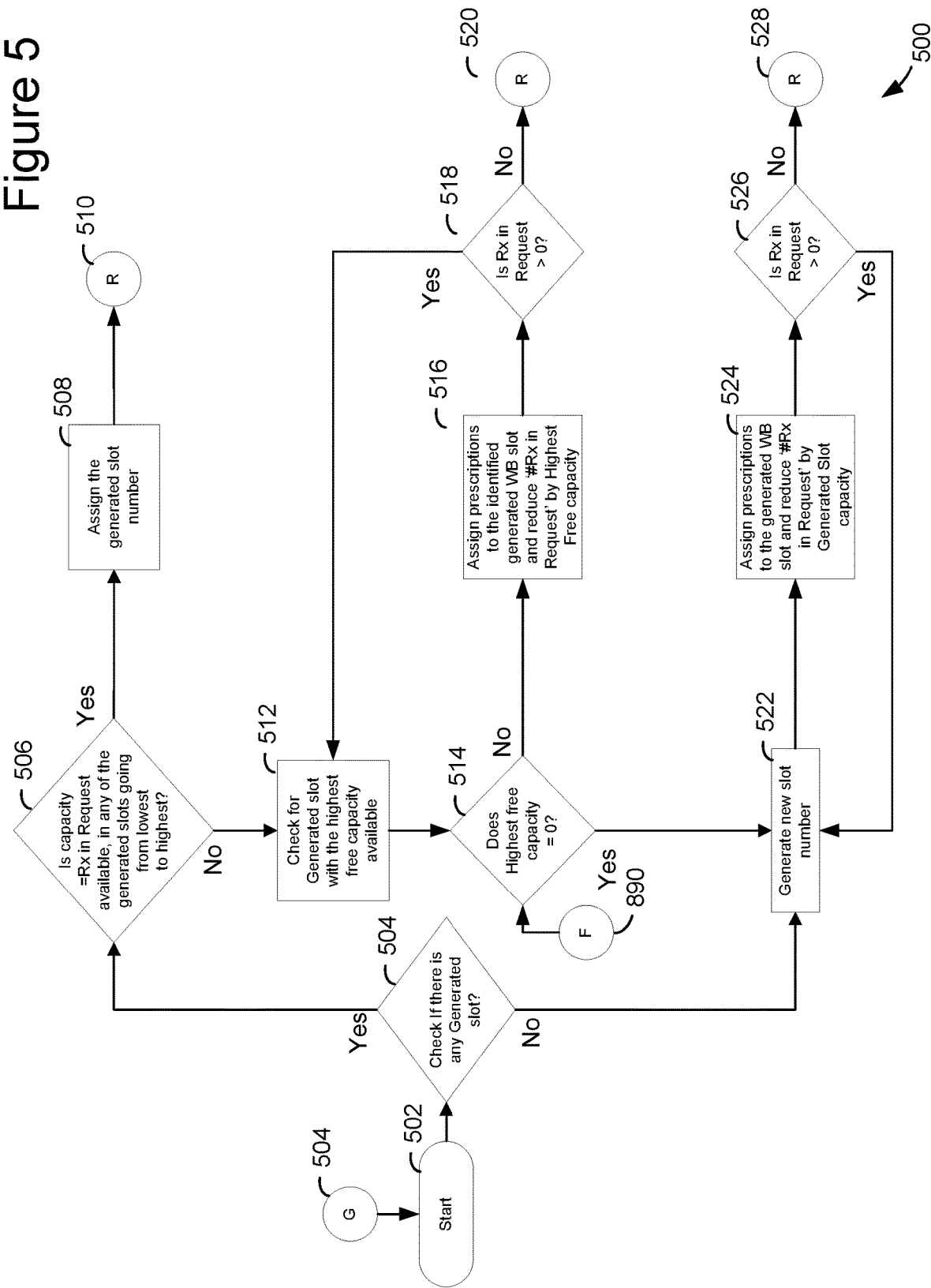
FIG. 5 is a flowchart of an example method for generating waiting bin slots.

FIG. 5 describes an example method 500 of generating bin slots for a prescription in a prescription request, such as the prescription requests processed through a prescription fulfillment workflow. In some embodiments, method 500 may be executed by a waiting bin engine, such as numeric waiting bin engine 330 in FIG. 3. Computer-based method steps may be executed by one or more computing systems, such as computing device 300 and/or one or more of the components of system 100. In some embodiments, the blocks of method 500 may correspond to capacity rules evaluated by a rules engine in the computing system. In some embodiments, method 500 may be responsive to an outcome of method 400 where additional waiting bin capacity needs to be allocated for an active group of prescriptions in a prescription request.

Method 500 may start at 502. At 506, a check may be performed to determine whether there are any generated slots. For example, method 500 may have previously generated slots by assigning serial identifiers that have not yet had prescriptions allocated to them or generates slots may have been recovered after all prescriptions in those slots were picked up or otherwise disposed of and the waiting bin engine may check the bin log to identify generated but inactive bins. If yes, there is one or more generated slots and method 500 may proceed to 506. If no, there are no generated slots available and method 500 may proceed to 522.

At 506, the capacity of the generated slots may be compared to the prescription requests. For example, the waiting bin engine may evaluate whether the prescriptions in the request equal the capacity of any of the generated slots going from lowest to highest. If yes, a generated slot is available with capacity for the prescriptions and method 500 may proceed to 508. If no, there is no slot equal to the prescriptions in request and method 500 may proceed to 512.

At 508, the generated slot number may be assigned. For example, the waiting bin engine may assign the generated slot number to the prescriptions in request. Through 510 and 420, method 500 may proceed to 422 in FIG. 4 to send the slot serial identifier as described above.

At 512, generated slots may be checked for the generated slot with the highest free capacity available. For example, the waiting bin engine may check each of the generated slots for highest available capacity for assigning prescriptions until the highest free capacity reaches 0. At 514, highest free capacity is evaluated. For example, the waiting bin engine may determine whether the highest free capacity has reached zero. If no, capacity is available and method 500 may proceed to 516. If yes, available capacity for the generated slots has reached 0 and method 500 may proceed to 522.

At 516, bin identifiers for the generated slot may be assigned to prescriptions and the prescriptions in the request may be reduced. For example, the waiting bin engine may assign the generated bin with highest available free capacity (greater than 0) identified at 512 to one or more prescriptions and the number of prescriptions in the request may be reduced by the number of prescriptions assigned, generally equal to the highest free capacity. At 518, the number of prescriptions in the request may be checked to determine whether additional prescriptions still need bin assignments. If no, the number of prescriptions in request has reached zero and method 500 may proceed through 520 and 420 to 422 as described above. If yes, the number of prescriptions is greater than zero and method 500 may return to 512.

At 522, a new slot number may be generated. For example, the waiting bin engine may assign a next serial identifier up to the number of bins value in the waiting bin configuration for a next physical bin.

At 524, bin identifiers for the generated slot may be assigned to prescriptions and the prescriptions in the request may be reduced. For example, the waiting bin engine may assign the newly generated bin from 522 to one or more prescriptions and the number of prescriptions in the request may be reduced by the number of prescriptions assigned. At 526, the number of prescriptions in the request may be checked to determine whether additional prescriptions still need bin assignments. If no, the number of prescriptions in request has reached zero and method 500 may proceed through 528 and 420 to 422 as described above. If yes, the number of prescriptions is greater than zero and method 500 may return to 522 to generate additional serial identifiers for additional physical bins.

Figure 6:
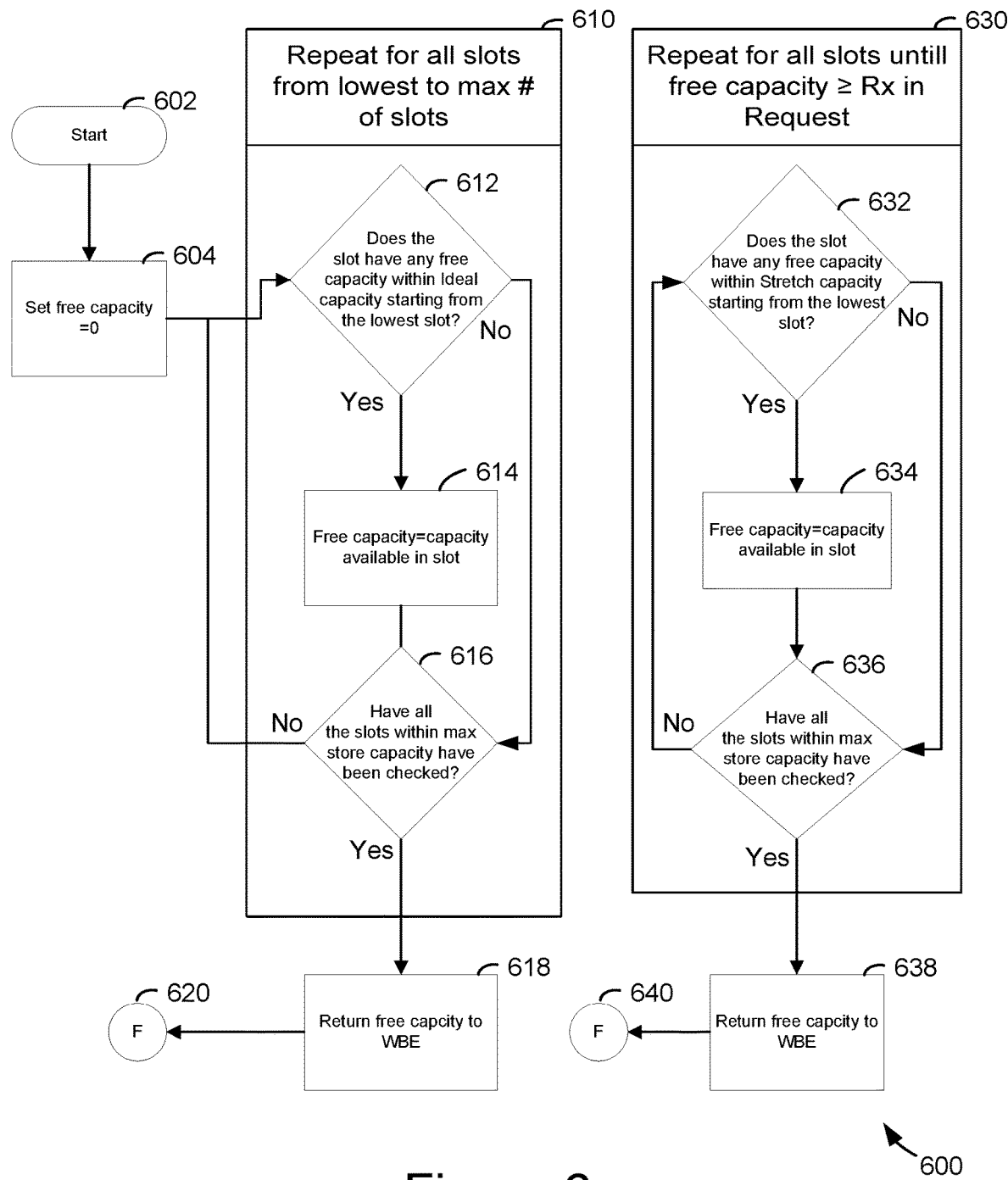
FIG. 6 is flowcharts of an example method for determining free preferred and stretch capacity.
Figure 7:
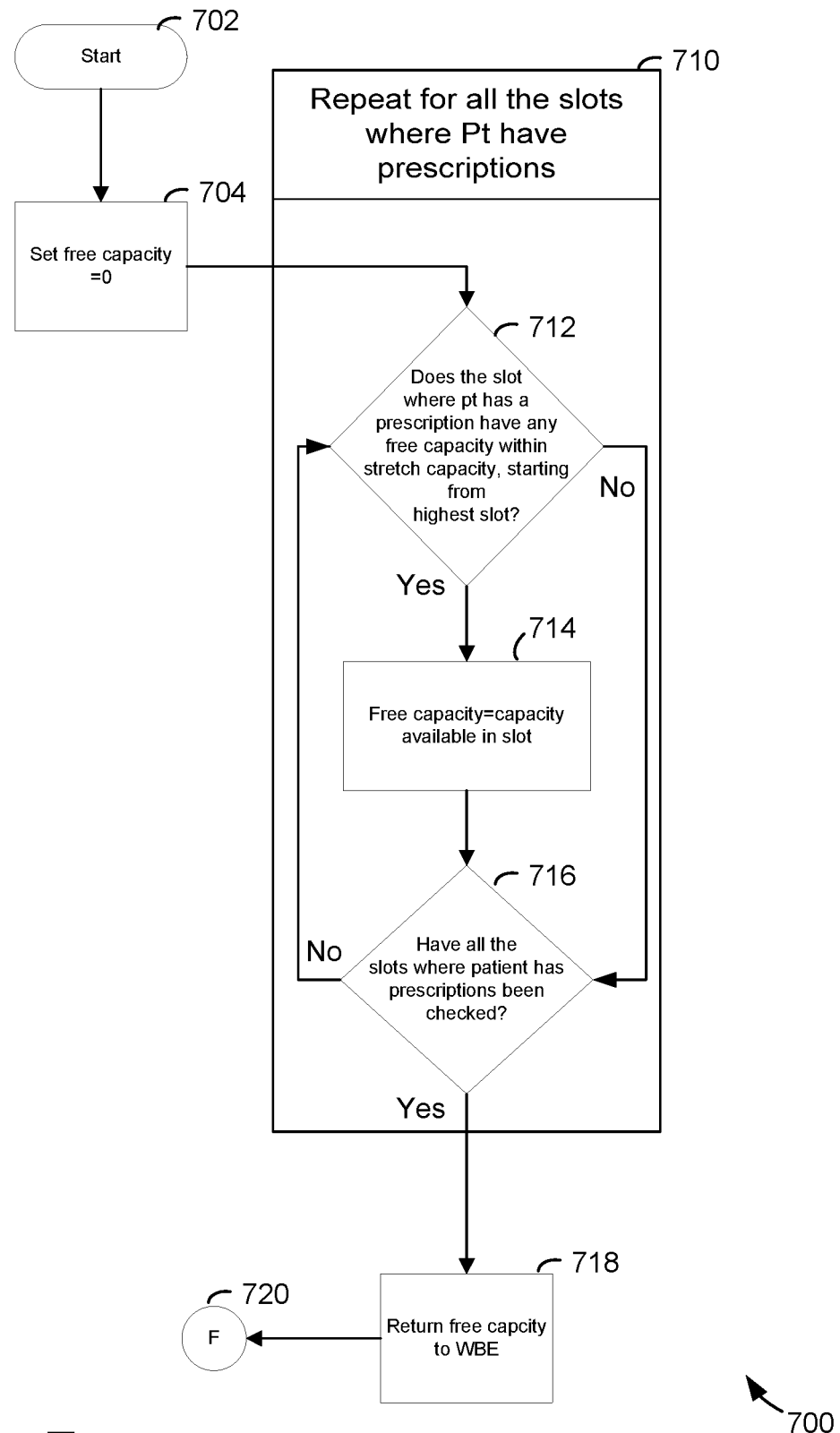
FIG. 7 is a flowchart of an example method for determining free capacity collocated with other prescriptions.
Figure 8:
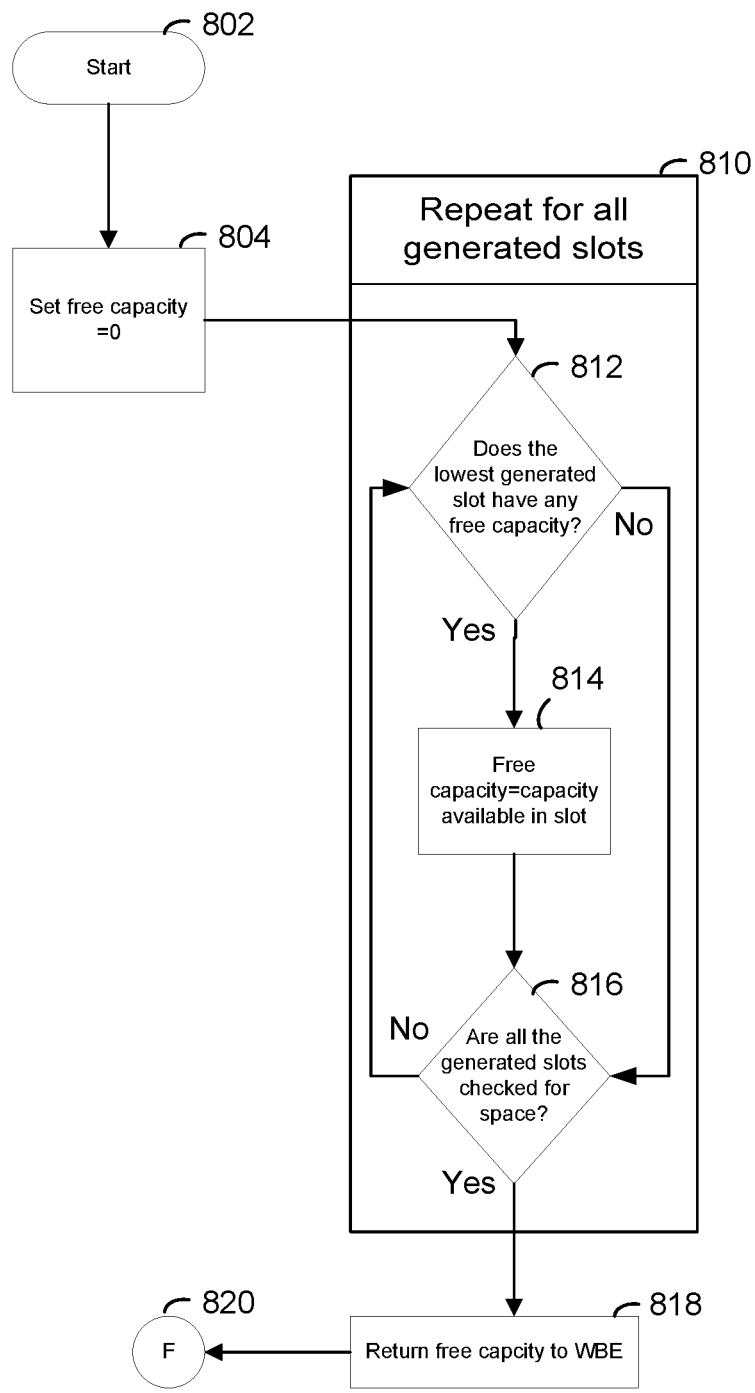
FIG. 8 is a flowchart of an example method for determining free capacity from generated slots.

FIGS. 6-8 describe example methods 600, 700, and 800 of calculating free capacity for use in assigning new prescriptions to specific slots in the waiting bins. In some embodiments, methods 600, 700, and 800 may be executed by a waiting bin engine, such as numeric waiting bin engine 330 in FIG. 3. Computer-based method steps may be executed by one or more computing systems, such as computing device 300 and/or one or more of the components of system 100. In some embodiments, the blocks of methods 600, 700, and/or 800 may correspond to subroutines supporting assignment rules evaluated by a rules engine in the computing system. In some embodiments, methods 600, 700, and 800 may be executed as background processes, such as by a recovery module, to provide periodic or event-based recalculation of free capacity. For example, method 600 may be initiated by pickup events and current free capacity values may be calculated and stored in a bin log or another data structure for use in evaluating assignment rules.

Method 600 may start at 602. In some embodiments, method 600 may be initiated during one or more checks for free capacity in method 400. At 604, free capacity may be set to zero. For example, one or more free capacity values may be requested by an available capacity check, such as a preferred capacity check and/or a stretch capacity check, and the free capacity value for the check may initially be set to equal zero.

In some embodiments, method 600 may execute subroutine 610 for checking available capacity using ideal or preferred capacity values from the bin configuration. For example, a capacity check may initially be made to attempt to place prescriptions in slots with available capacity under their preferred capacity. In some embodiments, subroutine 610 may be repeated for all slots or slot serial identifiers from a lowest value to a maximum number of active slots.

At 612, whether a slot has free capacity under its preferred capacity value may be determined. For example, the aggregate number and/or size of prescriptions assigned to a particular slot serial identifier may be determined from the bin log and compared against the preferred capacity value for the bin configuration and a difference may indicate that the slot has free capacity. If yes, the free capacity of the slot is greater than zero and method 600 may proceed to 614. If no, the free capacity of the slot is zero (or less if stretch capacity has been used) and method 600 may proceed to 616.

At 614, free capacity may be set to reflect the available capacity. For example, the free capacity value may be set to equal the free capacity value calculated from the comparison at 612. In some embodiments, 614 may return only a single free capacity value, a highest free capacity value, an aggregate free capacity value, and/or an array of free capacity values.

At 616, whether all slots have been checked may be evaluated. For example, the waiting bin engine may repeat 612 and 614 until the maximum serial identifier has been checked, up to store capacity reflected in the number of bins value in the bin configuration. If yes, all slots have been evaluated and method 600 may proceed to 618. If no, slots remain to be evaluated and method 600 may return to 612. At 618, free capacity may be returned. For example, one or more free capacity values and corresponding slot serial numbers may be returned through 620 and 690 to 478 in FIG. 4B.

In some embodiments, method 600 may execute subroutine 630 for checking available capacity using stretch capacity values from the bin configuration. For example, a capacity check may be made to attempt to place prescriptions in slots with available capacity under their stretch capacity after insufficient capacity is found within ideal or preferred capacities. In some embodiments, subroutine 630 may be repeated for all slots or slot serial identifiers from a lowest value to a maximum number of active slots or until free capacity equals or exceeds the number or size of the prescriptions in the request.

At 632, whether a slot has free capacity under its stretch capacity value may be determined. For example, the aggregate number and/or size of prescriptions assigned to a particular slot serial identifier may be determined from the bin log and compared against the stretch capacity value for the bin configuration and a difference may indicate that the slot has free capacity. If yes, the free capacity of the slot is greater than zero and method 600 may proceed to 634. If no, the free capacity of the slot is zero (or less if stretch capacity has been used) and method 600 may proceed to 636.

At 634, free capacity may be set to reflect the available capacity. For example, the free capacity value may be set to equal the free capacity value calculated from the comparison at 632. In some embodiments, 634 may return only a single free capacity value, a highest free capacity value, an aggregate free capacity value, and/or an array of free capacity values.

At 636, whether all slots have been checked may be evaluated. For example, the waiting bin engine may repeat 632 and 634 until the maximum serial identifier has been checked, up to store capacity reflected in the number of bins value in the bin configuration. If yes, all slots have been evaluated and method 600 may proceed to 638. If no, slots remain to be evaluated and method 600 may return to 632. At 638, free capacity may be returned. For example, one or more free capacity values and corresponding slot serial numbers may be returned through 640 and 692 to 492 in FIG. 4C.

Method 700 may start at 702. In some embodiments, method 700 may be initiated during one or more checks for free capacity in method 400. At 704, free capacity may be set to zero. For example, one or more free capacity values may be requested by an available capacity check specific to slots with a previously assigned prescription for the same patient or group and the free capacity value for the check may initially be set to equal zero.

In some embodiments, method 700 may execute subroutine 710 for checking available capacity using stretch capacity values from the bin configuration for a subset of bins. For example, a subset of slot serial identifiers containing previously assigned prescriptions for the same patient or group of related prescriptions may be identified and checked. In some embodiments, subroutine 710 may be repeated for all slots or slot serial identifiers that contain prescriptions with the same patient identifier or another group identifier, starting at the highest slot and proceeding down.

At 712, whether a slot has free capacity under its stretch capacity value may be determined. For example, the aggregate number and/or size of prescriptions assigned to a particular slot serial identifier may be determined from the bin log and compared against the stretch capacity value for the bin configuration and a difference may indicate that the slot has free capacity. If yes, the free capacity of the slot is greater than zero and method 700 may proceed to 714. If no, the free capacity of the slot is zero (or less if stretch capacity has been used) and method 700 may proceed to 716.

At 714, free capacity may be set to reflect the available capacity. For example, the free capacity value may be set to equal the free capacity value calculated from the comparison at 712. In some embodiments, 714 may return only a single free capacity value, a highest free capacity value, an aggregate free capacity value, and/or an array of free capacity values.

At 716, whether all slots have been checked may be evaluated. For example, the waiting bin engine may repeat 712 and 714 until all slots containing prescriptions for that patient identifier or group have been checked. If yes, all slots have been evaluated and method 700 may proceed to 718. If no, slots remain to be evaluated and method 700 may return to 712. At 718, free capacity may be returned. For example, one or more free capacity values and corresponding slot serial numbers may be returned through 720 and 790 to 460 in FIG. 4B.

Method 800 may start at 802. In some embodiments, method 800 may be initiated during one or more checks for free capacity in method 500. At 804, free capacity may be set to zero. For example, one or more free capacity values may be requested by an available capacity check for generated slots and the free capacity value for the check may initially be set to equal zero.

In some embodiments, method 800 may execute subroutine 810 for checking available capacity using preferred capacity values from the bin configuration for generated bin slots. For example, one or more newly generated bins with assigned slot serial identifiers may be identified and checked. In some embodiments, subroutine 810 may be repeated for all slots or slot serial identifiers generated by a slot generation method, such as method 500, starting at the lowest generated slot and proceeding upward.

At 812, whether a slot has free capacity under its preferred capacity value may be determined. For example, the aggregate number and/or size of prescriptions assigned to a particular slot serial identifier may be determined from the bin log and compared against the preferred capacity value for the bin configuration and a difference may indicate that the slot has free capacity. If yes, the free capacity of the slot is greater than zero and method 800 may proceed to 814. If no, the free capacity of the slot is zero (or less if stretch capacity has been used) and method 800 may proceed to 816.

At 814, free capacity may be set to reflect the available capacity. For example, the free capacity value may be set to equal the free capacity value calculated from the comparison at 812. In some embodiments, 814 may return only a single free capacity value, a highest free capacity value, an aggregate free capacity value, and/or an array of free capacity values.

At 816, whether all slots have been checked may be evaluated. For example, the waiting bin engine may repeat 812 and 814 until all newly generated slots have been checked. If yes, all slots have been evaluated and method 800 may proceed to 818. If no, slots remain to be evaluated and method 800 may return to 812. At 818, free capacity may be returned. For example, one or more free capacity values and corresponding slot serial numbers may be returned through 820 and 890 to 514 in FIG. 5.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

To ease description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and Modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats.

Furthermore, the modules, routines, features, attributes, methodologies and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

What is claimed is:

1. A system comprising:
   at least one processor;
   at least one memory;
   a graphical user interface; and
   a numeric waiting bin engine stored in the at least one memory and executable by the at least one processor to:
      receive a plurality of bin configuration values, wherein the bin configuration values include:
         a number of bins value; and
         a preferred capacity value;
      store the plurality of bin configuration values in a bin configuration file in non-volatile storage;
      assign a plurality of serial identifiers to a plurality of physical bins using the bin configuration values, wherein each physical bin of the plurality of physical bins receives a unique serial identifier from the plurality of serial identifiers;
      selectively assign a slot serial identifier from the plurality of serial identifiers to a selected prescription, wherein the selected prescription has a size value and the size value is less than the preferred capacity value; and
      display, responsive to a request for the selected prescription, the slot serial identifier for the selected prescription on the graphical user interface.

2. The system of claim 1, further comprising:
   a label printer for prescriptions, wherein:
      the numeric waiting bin engine is further executable to transmit the slot serial identifier for the selected prescription to the label printer; and
      the label printer is configured to print the slot serial identifier on a prescription label affixed to the selected prescription.

3. The system of claim 1, further comprising:
   a point of sale system configured to:
      receive the request for the selected prescription;
      access a prescription record for the selected prescription, wherein the numeric waiting bin engine is further executable to store the slot serial identifier for the selected prescription in the prescription record for the selected prescription;
      determine the slot serial identifier from the prescription record; and
      display the slot serial identifier for the selected prescription on a graphical user interface of the point of sale system.

4. The system of claim 1, wherein:
   the bin configuration values further include a stretch capacity value; and
   the numeric waiting bin engine is further executable to selectively assign the slot serial identifier from the plurality of serial identifiers to the selected prescription, wherein the size value of the selected prescription:
      exceeds the preferred capacity value; and
      does not exceed the stretch capacity value.

5. The system of claim 1, wherein:
   the plurality of physical bins includes an oversized area for bulk storage;
   the bin configuration values further include a bulk capacity value; and
   the numeric waiting bin engine is further executable to selectively assign the slot serial identifier from the plurality of serial identifiers to the selected prescription, wherein the size value of the selected prescription exceeds the bulk capacity value.

6. The system of claim 1, wherein:
   the selected prescription has an associated drug classification identifier;
   the associated drug classification identifier indicates at least one special handling category selected from: refrigerate, reconstitute, immunization, controlled, and excluded; and
   the numeric waiting bin engine is further executable to selectively assign the slot serial identifier from the plurality of serial identifiers to the selected prescription using at least one fixed slot serial identifier corresponding to a storage location based on the associated drug classification identifier.

7. The system of claim 1, wherein:
   the plurality of physical bins includes a plurality of sets of bins having different sizes;
   the bin configuration values include a plurality of bin configuration sets;
   each bin configuration set of the plurality of bin configuration sets corresponds to a set of bins of equal size from the plurality of sets of bins;
   each bin configuration set includes the number of bins value and the preferred capacity value for the corresponding set of bins of equal size; and
   the numeric waiting bin engine is further executable to selectively assign the slot serial identifier from the plurality of serial identifiers to the selected prescription, wherein the size value of the selected prescription:
      exceeds the preferred capacity value of a first bin configuration set; and
      does not exceed the preferred capacity value of a second bin configuration set, the slot serial identifier associated with a bin corresponding to the second bin configuration set.

8. The system of claim 1, further comprising:
   a bin log file stored in the at least one memory, the bin log file including prescription identifiers and size values for each serial identifier from the plurality of serial identifiers with at least one assigned prescription, wherein the numeric waiting bin engine is further executable to:
      access, responsive to a prescription fulfillment workflow, the bin log file;
      process the bin log file using the size value to determine available slots from the plurality of serial identifiers with at least one assigned prescription, wherein the slot serial identifier is selectively assigned from the available slots;
      add, responsive to no slots from the plurality of serial identifiers with at least one assigned prescription accommodating the selected prescription, a new serial identifier for a next sequential bin not exceeding the number of bins value; and
      selectively assign the new serial identifier as the slot serial identifier for the selected prescription.

9. The system of claim 1, further comprising:
   a rules engine, stored in the at least one memory for execution by the at least one processor, configured to process a plurality of assignment rules for selectively assigning the slot serial identifier to the selected prescription, wherein:
      the plurality of assignment rules is selected from predetermined assignment rules, slot availability checking rules, capacity checking rules, bin generation rules, and bin recovery rules; and the numeric waiting bin engine is further executable to:
evaluate, responsive to a prescription fulfillment workflow, the plurality of assignment rules using the rules engine and at least one value from a prescription record for the selected prescription; and
determine, responsive to evaluating the plurality of assignment rules, the slot serial identifier to be selectively assigned to the selected prescription.

10. The system of claim 9, wherein:
the plurality of assignment rules includes grouping logic rules;
evaluating the plurality of assignment rules includes:
identifying a plurality of related prescriptions, including the selected prescription;
evaluating at least one grouping logic rule to determine whether the plurality of related prescriptions may be assigned to the slot serial identifier; and
evaluating at least one grouping logic rule to determine whether the plurality of related prescriptions may be assigned to a sequential set of serial identifiers including the slot serial identifier; and
determining the slot serial identifier locates the plurality of related prescriptions as a group in the plurality of physical bins.

11. A computer-based method comprising:
receiving, through a computer interface of a computing system, a plurality of bin configuration values corresponding to a plurality of physical bins, wherein the bin configuration values include:
a number of bins value; and
a preferred capacity value;
storing the plurality of bin configuration values in a bin configuration file in non-volatile storage of the computing system;
assigning a plurality of serial identifiers to the plurality of physical bins using the bin configuration values, wherein each physical bin of the plurality of physical bins receives a unique serial identifier from the plurality of serial identifiers;
selectively assigning a slot serial identifier from the plurality of serial identifiers to a selected prescription, wherein the selected prescription has a size value and the size value is less than the preferred capacity value; and
displaying, responsive to a request for the selected prescription, the slot serial identifier for the selected prescription on a graphical user interface of the computing system.

12. The computer-based method of claim 11, further comprising:
transmitting the slot serial identifier for the selected prescription to a label printer of the computing system; and
printing, using the label printer, the slot serial identifier on a prescription label affixed to the selected prescription.

13. The computer-based method of claim 11, further comprising:
storing, by a pharmacy management system connected to the computing system, the slot serial identifier for the selected prescription in a prescription record for the selected prescription;
receiving the request for the selected prescription at a point of sale system connected to the computing system;
accessing the prescription record for the selected prescription from the pharmacy management system;
determining the slot serial identifier from the prescription record; and
displaying the slot serial identifier for the selected prescription on a graphical user interface of the point of sale system.

14. The computer-based method of claim 11, further comprising:
receiving, through the computer interface of the computing system, a stretch capacity value from the bin configuration values;
evaluating whether the size value exceeds the preferred capacity value of available slots of the plurality of serial identifiers;
evaluating, responsive to determining the size value does exceed the preferred capacity value of available slots of the plurality of serial identifiers, whether the size value exceeds the stretch capacity value; and
selecting, responsive to determining the size value does not exceed the stretch capacity value, the slot serial identifier.

15. The computer-based method of claim 11, further comprising:
determining an associated drug classification identifier for the selected prescription, wherein the associated drug classification identifier indicates at least one special handling category selected from: refrigerate, reconstitute, immunization, controlled, and excluded; and
selecting the slot serial identifier from the plurality of serial identifiers for the selected prescription using at least one fixed slot serial identifier corresponding to a storage location based on the associated drug classification identifier.

16. The computer-based method of claim 11, further comprising:
receiving, through the computer interface of the computing system, a plurality of bin configuration sets, wherein:
each bin configuration set of the plurality of bin configuration sets corresponds to a set of physical bins of equal size from the plurality of physical bins; and
each bin configuration set includes the number of bins value and the preferred capacity value for the corresponding set of bins of equal size;
evaluating whether the size value exceeds the preferred capacity value of available slots of a first bin configuration set;
evaluating, responsive to determining the size value does exceed the preferred capacity value of available slots of the first bin configuration set, whether the size value exceeds the preferred capacity value of available slots of a second bin configuration set; and
selecting, responsive to determining the size value does not exceed the preferred capacity value of available slots of the second bin configuration set, the slot serial identifier from the second bin configuration set.

17. The computer-based method of claim 11, further comprising:
storing a bin log file in the computer system, wherein the bin log file includes prescription identifiers and size values for each serial identifier from the plurality of serial identifiers with at least one assigned prescription;
accessing, responsive to a prescription fulfillment workflow, the bin log file; and processing the bin log file using the size value to determine available slots from the plurality of serial identifiers with at least one assigned prescription, wherein the slot serial identifier is selectively assigned from the available slots.

18. The computer-based method of claim 17, further comprising:

adding, responsive to no slots from the plurality of serial identifiers with at least one assigned prescription accommodating the selected prescription, a new serial identifier for a next sequential bin not exceeding the number of bins value; and selecting the new serial identifier as the slot serial identifier for the selected prescription.

19. The computer-based method of claim 11, further comprising:

evaluating, using a rules engine to process a plurality of logical rules for selectively assigning the slot serial identifier to the selected prescription, a plurality of assignment rules using at least one value from a prescription record for the selected prescription; and selecting, responsive to evaluating the plurality of assignment rules, the slot serial identifier to be selectively assigned to the selected prescription, wherein the plurality of assignment rules is selected from predetermined assignment rules, slot availability checking rules, capacity checking rules, bin generation rules, bin recovery rules, and grouping logic rules.

20. A computing system comprising:

at least one processor;

at least one memory;

a graphical user interface;

non-volatile storage storing a plurality of bin configuration values corresponding to a plurality of physical bins configured to receive and store prescriptions for customer pick-up, wherein the bin configuration values include:

a number of bins value;

a preferred capacity value; and a stretch capacity value; and a numeric waiting bin engine stored in the at least one memory and executable by the at least one processor to:

assign a plurality of serial identifiers to the plurality of physical bins using the bin configuration values, wherein each physical bin of the plurality of physical bins receives a unique serial identifier from the plurality of serial identifiers;

evaluate, using a rules engine to process a plurality of logical rules for selectively assigning a slot serial identifier to a selected prescription, a plurality of assignment rules based on the preferred capacity value and the stretch capacity value;

select, responsive to evaluating the plurality of assignment rules, the slot serial identifier for the selected prescription; and display, responsive to a request for the selected prescription, the slot serial identifier for the selected prescription on the graphical user interface.

* * * * *